(12) United States Patent
Shi et al.

(10) Patent No.: US 10,399,971 B2
(45) Date of Patent: Sep. 3, 2019

(54) COMPOUND FOR TREATING OR PREVENTING HYPERURICEMIA OR GOUT

(71) Applicant: JIANGSU ATOM BIOSCIENCE AND PHARMACEUTICAL CO., LTD., Zhenjiang (CN)

(72) Inventors: Dongfang Shi, Fremont, CA (US); Changjin Fu, Zhenjiang (CN); Xi Cheng, Zhenjiang (CN); Jianghua Zhu, Zhenjiang (CN); Jie Wen, Zhenjiang (CN); Jie Gu, Zhenjiang (CN)

(73) Assignee: JIANGSU ATOM BIOSCIENCE AND PHARMACEUTICAL CO., LTD., Zhenjiang (CN)

(*) Notice: Subject to any disclaimer, the term of this patent is extended or adjusted under 35 U.S.C. 154(b) by 1 day.

(21) Appl. No.: 15/758,866

(22) PCT Filed: Sep. 8, 2016

(86) PCT No.: PCT/CN2016/098468
§ 371 (c)(1),
(2) Date: Mar. 9, 2018

(87) PCT Pub. No.: WO2017/041732
PCT Pub. Date: Mar. 16, 2017

(65) Prior Publication Data
US 2018/0282321 A1   Oct. 4, 2018

(30) Foreign Application Priority Data
Sep. 10, 2015  (CN) .......................... 2015 1 0576110

(51) Int. Cl.
C07D 471/04 (2006.01)
A61K 31/437 (2006.01)
A61P 19/06 (2006.01)

(52) U.S. Cl.
CPC .......... C07D 471/04 (2013.01); A61K 31/437 (2013.01); A61P 19/06 (2018.01)

(58) Field of Classification Search
CPC .................................................. C07D 471/04
USPC ........................................ 546/121; 514/300
See application file for complete search history.

(56) References Cited

PUBLICATIONS

Moog et al., "Bicyclic imidazo, etc.," Antiviral Research 24, 275-288. (Year: 1994).*
Gubin et al., "Preparation of, etc.," CA 115:8801. (Year: 1991).*
Price et al., "Human Vascular, etc.," J of the American Society of Nephrology, 17, 1791-1795. (Year: 2006).*
Tassone et al., "Uric Acid Impairs, etc.," Frontiers in Endocrinology,9, 1-7. (Year: 2018).*
Gliozzi et al., "The treatment, etc," International Journal of Cardiology, 213, 23-27.. (Year: 2013).*
Sattui et al., "Treatment of hyperricemia, etc.," Therapeutic Advances in Musculoskeletal Disease, 8(4), 145-159. (Year: 2016).*

* cited by examiner

*Primary Examiner* — Patricia L Morris
(74) *Attorney, Agent, or Firm* — CBM Patent Counsulting, LLC

(57) ABSTRACT

The invention discloses a class of compounds for treating or preventing hyperuricemia or gout, which is a compound shown in general formula (I) or a pharmaceutically acceptable salt. These compounds and their pharmaceutically acceptable salts in the invention are useful for the promotion of uric acid excretion to treat or prevent hyperuricemia or gout.

9 Claims, No Drawings

COMPOUND FOR TREATING OR PREVENTING HYPERURICEMIA OR GOUT

TECHNICAL FIELD

This invention belongs to the field of medicinal chemistry and particularly relates to a class of (4-hydroxyphenyl)(imidazo[1,2-a]pyridin-3-yl)methanone derivatives, their compositions, and their applications in medicine.

BACKGROUND OF THE INVENTION

Gout is a metabolic disease caused by chronically elevated serum uric acid (sUA) levels (hyperuricemia) due to the disorder of purine metabolism and/or from insufficient renal elimination of uric acid. Deposition of the needle-like crystals of urate in the joints leads to painful inflammatory arthritis. Hyperuricemia, defined as sUA concentration higher or equal to 6.8 mg/dL, may result in the precipitation of urate as mono-sodium salt in the synovial fluid of the human soft tissue, the cartilage of the peripheral joint, the auricle of the ear, and the olecranon bursa of the elbow. When such symptoms are presents, it can be diagnosed as gout. (Terkeltaub R A. Crystal Deposition Diseases. In: Goldman L, Aus-iello D, eds. The Cecil Textbook of Medicine, 23rd ed. Philadelphia, Pa.: Saunders Elsevier Co; 2008:2069-2075; Richette P, Bardin T. Gout. Lancet. 2010, 375(9711):318-328)

Gout is the common type of inflammatory arthritis and has an incidence of approximately 1%-2%. The incidence in the developed countries is relatively high, as a survey of 2007-2008 reported there were about 8.3 million of gout patients in the US. In China, the incidence of gout has dramatically increased in the past decade. It is reported that the number of gout patients in China has exceeded 50 million, and the proportion of men with gout is much higher than that of women.

In the present, gout medications involve short-term treatment for pain relief and reduction of inflammation during an acute attack, the inhibition of uric acid production, and the promotion of uric acid excretion. Medicine for the treatment of acute attack of gout mainly include colchicine, non-steroidal anti-inflammatory drugs (NSAIDs), adrenocorticotropic hormone, and glucocorticoid.

Long-term medications of gout involve decreasing the formation of uric acid and/or increasing uric acid renal excretion. Allopurinol and uloric are the more often used drugs on decreasing the formation of uric acid. The mechanism of these drugs is to reduce the formation of uric acid by inhibiting the xanthine oxidase needed for the transformation of purine to uric acid. Uricosurics are the second class of urate lowering therapy currently available, which act by increasing uric acid renal elimination. They mainly include probenecid, sulphinpyrazone, and benzbromarone etc.

The treatment of acute gout attacks can only control the symptoms and relieve the pain of the patients, but it cannot reduce the concentration of sUA. Colchicine is very toxic, often accompanied by common adverse reactions such as diarrhea, vomiting and abdominal pain spasms. Allopurinol is one of the xanthine oxidase inhibitors. It needs to be used in high dose, and for some people can cause fatal Stevens Johnson syndrome (skin erythema multiforme), often accompanied by stomach discomfort, nausea, diarrhea, headache, fever, loss of appetite, weight loss, pain in urination, hematuria and other side effects. Another xanthine oxidase inhibitor is called uloric (febuxostat), which was launched in Europe and the US in 2009. Although uloric shows good efficacy in lowering uric acid levels in the body, it also has very serious side effects such as cardiovascular problem and gastrointestinal discomfort, potentially causing headaches and liver injury. Benzbromarone has a good uricosuric efficacy, but it leads to fatal liver injury. Both probenecid and sulfinpyrazone are uricosuric agents with high dose administration in poor efficacy and bad side effects.

The mechanism of uricosurics involves the inhibition of the re-absorption of uric acid in the proximal tubular cells to increase the renal excretion of uric acid and reduce the concentration of blood uric acid. About 70% of uric acid excretion in human is by the kidneys, and about 80-85% of hyperuricemia patients is caused by uric acid excretion disorder. (Cheeseman C. Solute carrier family 2, member 9 and uric acid homeostasis. Current Opinion in Nephrology and Hypertension, 2009, 18 (5): 428-432)

Uric acid excretion plays a very important role in the treatment of hyperuricemia and gout. Human urate anion transporter 1 (hURAT1) is located in the proximal tubular epithelial cell membrane, and it belongs a super family member of an organic anion transporter (OAT), which is encoded by SLC22A12 gene. Its cDNA has several mutations that cause uric acid metabolism abnormally. A Meta analysis showed that this gene has 0.13% variables contributed to serum uric acid level. (So A, Thorens B. Uric acid transport and disease. Journal of Clinical Investigation., 2010, 120 (6): 1791-1799)

The URAT1 controls more than 90% of the uric acid re-absorption after glomerular filtration. Therefore, selective inhibition of URAT1 can decrease the re-absorption of uric acid and promote the excretion of uric acid in the kidneys to reduce uric acid levels in the body. (Michael F W, Jutabha P, Quada B. Developing potent human uric acid transporter 1 (hURAT1) inhibitors. Journal of Medicinal Chemistry. 2011, 54:2701-2713)

Currently, benzbromarone as the URAT1 inhibitor is still widely used in the market for the treatment of gout. Its chemical name is (3,5-dibromo-4-hydroxyphenyl)(2-ethylbenzofuran-3-yl)methanone, which was developed by France Snaofi-Synthelabo company and launched in 1976. It is the most effective uricosuric agent in the market and has been used for nearly 40 years. But the use of benzbromarone has not been approved in the US and was withdrawn from most European markets in 2003 due to its side effect of severe liver toxicity. (Jansen T L, Reinders M K, van Roon E N, et al. Benzbromarone withdrawn from the European market: another case of "absence of evidence is evidence of absence". Clinical Experimental Rheumatology, 2004, 22(5): 651) Another disadvantage is that it has a strong inhibitory effect on the liver CYP2C9 enzyme. However, more than 20 countries, such as China, Germany, Japan, Brazil, and New Zealand still widely use it because of the lack of good gout drugs on the market.

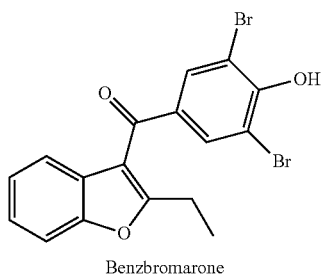 [SMILES: CCc1oc2ccccc2c1C(=O)c1cc(Br)c(O)c(Br)c1]

Benzbromarone

Studies have shown that the fulminant or fatal liver injury of benzbromarone has been associated with its reactive metabolites. A possible mechanism of liver toxicity may involve the bioactivation of benzbromarone through sequential hydroxylation of the benzofuran ring to form 6-hydroxybenzbromarone and a catechol by CYP2C9, which can be further oxidized by P450s enzymes to a reactive quinone metabolite capable of adducting thiol reagents/cysteine residues. (Matthew G. McDonald, Rettie A E. Sequential metabolism and bioactivation of the hepatotoxin benzbromarone: formation of glutathione adducts from a catechol intermediate. Chemical Research in Toxicology. 2007, 20 (12):1833-1842)

Benzbromarone also has other side effects, such as diarrhea, stomach discomfort, nausea, digestive system symptoms, skin allergies such as macula, flush, itching, and so on.

Currently, severe side effects from either the uricosuric agents or xanthine oxidase inhibitors have greatly affected the long-term use of these gout medicines. Therefore, it is critical to develop gout drugs that are highly effective and have low toxicity.

BRIEF SUMMARY OF THE INVENTION

A class of novel (4-hydroxyphenyl)(imidazo[1,2-a]pyridin-3-yl)methanone derivatives as URAT1 inhibitors, methods for their preparation, and related synthetic intermediates and compositions are provided. The test results both in vitro and in vivo showed that compounds provided by this invention can significantly improve the inhibitory effect on URAT1, as well as significantly increase uric acid excretion in mice and reduce the toxicity to normal liver cells in comparison with benzbromarone. The oral maximum tolerated dose of acute toxicity test in rats showed that the toxicity of the compound provided by the invention was much lower than that of benzbromarone. The studies have shown that the compound provided by the invention is highly effective in uric acid excretion and has low toxicity.

Another purpose of the present invention is to provide a pharmaceutical composition containing (4-hydroxyphenyl)(imidazo[1,2-a]pyridin-3-yl)methanone derivatives.

Additionally, the compounds of (4-hydroxyphenyl)(imidazo[1,2-a]pyridin-3-yl) methanone described herein are useful in the prevention or treatment of hyperuricemia, nephropathy or gout.

Embodiments of the invention can be achieved by the following measures:

The compounds of the present invention are represented by Formula (I)

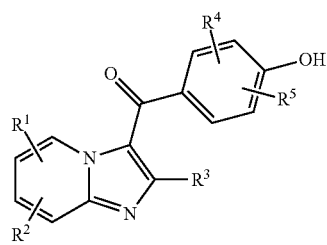

(I)

or a pharmaceutically acceptable salt thereof, wherein:

$R^1$ and $R^2$ are independently selected from the group consisting of hydrogen, deuterium, halogen, cyano, hydroxyl, $C_{1-5}$ alkyl, substituted $C_{1-5}$ alkyl, $C_{1-3}$ alkoxy, substituted $C_{1-3}$ alkoxy, $C_{1-3}$ alkylthio, or substituted $C_{1-3}$ alkylthio in one or more;

$R^3$ is selected from the substituted or unsubstituted group consisting of $C_{1-4}$ alkyl or $C_{3-4}$ cycloalkyl, and the substituents are independently selected from the group consisting of deuterium, halogen, $C_{1-2}$ alkyl or $C_{3-4}$ cycloalkyl.

$R^4$ and $R^5$ are independently selected from the group consisting of halogen, deuterium, cyano, $C_{2-3}$ alkenyl, $C_{2-3}$ alkynyl, $C_{1-3}$ alkyl, substituted $C_{1-3}$ alkyl, $C_{1-3}$ alkoxy, substituted $C_{1-3}$ alkoxy, $C_{1-3}$ alkylthio, or substituted $C_{1-3}$ alkylthio; wherein the substituents in $R^1$, $R^2$, $R^4$, and $R^5$ are independently selected from deuterium, halogen, $C_{1-3}$ alkyl, $C_{3-4}$ cycloalkyl or $C_{1-3}$ alkoxy.

$R^1$, $R^2$, $R^4$ and $R^5$ in the invention can be selected from one, two or more than two of the defined groups individually. When $R^1$, $R^2$, $R^4$ or $R^5$ are selected for two or more than two, these groups are located at the corresponding sites of phenyl ring or imidazo[1,2-a]pyridyl ring. For example, when $R^4$ uses two groups, the two groups can be at 2 and 3 positions in the 4-hydroxy phenyl, respectively.

In one embodiment, each $R^1$ or $R^2$ is independently selected from hydrogen, deuterium, halogen, cyano, hydroxyl, $C_{1-5}$ alkyl, substituted $C_{1-5}$ alkyl, $C_{1-3}$ alkoxy, substituted $C_{1-3}$ alkoxy, $C_{1-3}$ alkylthio, or substituted $C_{1-3}$ alkylthio; the substituents are selected from deuterium, halogen, $C_{1-3}$ alkyl, $C_{3-4}$ cycloalkyl or $C_{1-3}$ alkoxy.

In another preferred embodiment, $R^1$ and $R^2$ are independently selected from one or more of hydrogen, deuterium, fluorine, chlorine, bromine, cyano, hydroxyl, $C_{1-3}$ alkyl, substituted $C_{1-3}$ alkyl, $C_{1-3}$ alkoxy, or substituted $C_{1-3}$ alkoxy; the substituents are selected from deuterium, halogen, $C_{1-3}$ alkyl, $C_{3-4}$ cycloalkyl or $C_{1-3}$ alkoxy.

In some embodiments, $R^1$ or $R^2$ are independently selected from one or more of hydrogen, deuterium, fluorine, chlorine, bromine, cyano, $C_{1-3}$ alkyl, halogenated $C_{1-3}$ alkyl or $C_{1-3}$ alkoxy.

In some embodiments, $R^1$ and $R^2$ are independently selected from hydrogen, deuterium, fluorine, chlorine, bromine, cyano, methyl, ethyl, methoxy, ethoxy, trifluoromethyl and so on.

In some embodiments, $R^3$ is independently selected from $C_{1-3}$ alkyl, substituted $C_{1-3}$ alkyl, $C_{3-4}$ cycloalkyl or substituted $C_{3-4}$ cycloalkyl; The substituents are selected from deuterium, halogen, $C_{1-2}$ alkyl or $C_{3-4}$ cycloalkyl.

In some embodiments, $R^3$ is selected from $C_{2-3}$ alkyl or $C_{3-4}$ alkyl alkyl.

In some embodiments, $R^3$ is selected from ethyl or cyclopropyl.

In some embodiments, $R^4$ and $R^5$ are independently selected from hydrogen, deuterium, halogen, cyano, $C_{2-3}$ alkenyl, $C_{2-3}$ alkynyl, $C_{1-3}$ alkyl, substituted $C_{1-3}$ alkyl, $C_{1-3}$ alkoxy, substituted $C_{1-3}$ alkoxy, $C_{1-3}$ alkylthio or substituted $C_{1-3}$ alkylthio; the substituents are selected from deuterium, halogen, $C_{1-3}$ alkyl, $C_{3-4}$ cycloalkyl or $C_{1-3}$ alkoxy.

In some embodiments, $R^4$ and $R^5$ are independently selected from one or more of hydrogen, deuterium, halogen, cyano, ethylene, acetylene, $C_{1-2}$ alkyl, substituted $C_{1-2}$ alkyl, $C_{1-2}$ alkoxy, substituted $C_{1-2}$ alkoxy, $C_{1-2}$ alkylthio or substituted $C_{1-2}$ alkylthio; the substituents are selected from deuterium, halogen, $C_{1-2}$ alkyl, $C_{3-4}$ cycloalkyl or $C_{1-3}$ alkoxy.

In some embodiments, $R^4$ and $R^5$ are independently selected from one or more of hydrogen, deuterium, halogen, cyano, $C_{1-2}$ alkyl, halogenated $C_{1-2}$ alkyl, $C_{1-2}$ alkoxy or $C_{1-2}$ alkylthio.

In some embodiments, $R^4$ and $R^5$ are independently selected from one or more of hydrogen, deuterium, halogen, cyano, methyl, ethyl, methoxy, ethoxy, trifluoromethyl, methylthio or ethylthio.

In some embodiments, $R^4$ is selected from one or more of halogens, and $R^5$ is selected from cyano.

In some embodiments, "pharmaceutically acceptable salts" are salts formed by the compounds in the invention with acids, which are obtained by reacting free bases of the parent compounds with inorganic acids or organic acids, wherein the inorganic acids and the organic acids include (but not limited to): for example, hydrochloric acid, hydrobromic acid, nitric acid, phosphoric acid, acetic acid, propanoic acid, acrylic acid, oxalic acid, (D) or (L) malic acid, fumaric acid, maleic acid, hydroxybenzoic acid, γ-hydroxybutyric acid, methoxybenzoic acid, phthalic acid, methanesulfonic acid, ethanesulfonic acid, 1-naphthalenesulphonic acid, 2-naphthalenesulphonic acid, p-toluenesulfonic acid, salicylic acid, tartaric acid, citric acid and the like.

A compound of the present invention or its pharmaceutically acceptable salt, in which the compound is selected from:
(3,5-Dibromo-4-hydroxyphenyl)(2-ethylimidazo[1,2-a]pyridin-3-yl)methanone;
(2-Ethylimidazo[1,2-a]pyridine-3-yl)(4-hydroxy-3,5-diiodophenyl)methanone;
(3-Chloro-4-hydroxyphenyl)(2-ethylimidazo[1,2-a]pyridin-3-yl)methanone;
(3-Chloro-4-hydroxy-5-iodophenyl)(2-ethylimidazo[1,2-a]pyridin-3-yl)methanone;
3-Chloro-5-(2-ethylimidazo[1,2-a]pyridine-3-carbonyl)-2-hydroxybenzonitrile;
(3-Bromo-4-hydroxy-5-iodophenyl)(2-ethylimidazo[1,2-a]pyridine-3-yl)methanone;
(2-Ethylimidazo[1,2-a]pyridine-3-yl)(4-hydroxy-3-iodo-5-methylphenyl)methanone;
(2-Ethylimidazo[1,2-a]pyridine-3-yl)(4-hydroxy-3-iodophenyl)methanone;
5-(2-Ethylimidazo[1,2-a]pyridine-3-carbonyl)-2-hydroxybenzonitrile; (3-Chloro-4-hydroxyphenyl)(2-ethyl-6-fluoroimidazo[1,2-a]pyridin-3-yl)methanone; (3-Bromo-5-chloro-4-hydroxyphenyl)(2-ethyl-6-fluoroimidazo[1,2-a]pyridine-3-yl)methanone; (3-Chloro-4-hydroxy-5-iodophenyl)(2-ethyl-6-fluoroimidazo[1,2-a]pyridine-3-yl)methanone; 5-(2-Ethylimidazo[1,2-a]pyridine-3-carbonyl)-2-hydroxy-3-methylbenzonitrile; (2-Ethylimidazo[1,2-a]pyridine-3-yl)(4-hydroxy-3-(trifluoromethyl)phenyl)methanone; (3-Bromo-4-hydroxy-5-(trifluoromethyl)phenyl)(2-ethylimidazo[1,2-a]pyridine-3-yl)methanone;
(3,5-Dibromo-4-hydroxyphenyl)(2-ethyl-6-methylimidazo[1,2-a]pyridine-3-yl)methanone; (3,5-Dibromo-4-hydroxyphenyl)(2-ethyl-6-methoxyimidazo[1,2-a]pyridine-3-yl)methanone; 3-Bromo-5-(2-ethylimidazo[1,2-a]pyridine-3-carbonyl)-2-hydroxybenzonitrile; 5-(2-Ethylimidazo[1,2-a]pyridine-3-carbonyl)-2-hydroxy-3-iodobenzonitrile; 5-(2-Ethylimidazo[1,2-a]pyridine-3-carbonyl)-3-fluoro-2-hydroxybenzonitrile; (3,5-Dibromo-4-hydroxyphenyl)(2-propylimidazo[1,2-a]pyridine-3-yl)methanone;
(2-Ethylimidazo[1,2-a]pyridine-3-yl)(2-ethylsulfanyl-4-hydroxyphenyl)methanone; (3-Bromo-5-chloro-4-hydroxyphenyl)(2-ethylimidazo[1,2-a]pyridine-3-yl)methanone; (3-Bromo-5-fluoro-4-hydroxyphenyl)(2-ethyl-6-fluoroimidazo[1,2-a]pyridin-3-yl)methanone; (2-Ethyl-6-fluoroimidazo[1,2-a]pyridin-3-yl)(3-fluoro-4-hydroxy-5-iodophenyl)methanone; (3,5-Dibromo-4-hydroxyphenyl)(2-ethyl-6-hydroxyimidazo[1,2-a]pyridin-3-yl)methanone; (6-Bromo-2-ethyl-7-methylimidazo[1,2-a]pyridin-3-yl)(3,5-dibromo-4-hydroxyphenyl)methanone; (3,5-Dibromo-4-hydroxyphenyl)(2-ethyl-7-(trifluoromethyl)imidazo[1,2-a]pyridin-3-yl)methanone;
3-(3,5-Dibromo-4-hydroxyphenyl)-2-ethylimidazo[1,2-a]pyridine-6-carbonitrile; (2-Deuterium-4-hydroxyphenyl)(2-ethylimidazo[1,2-a]pyridine-3-yl)methanone; (2-Deuterium-3,5-dibromo-4-hydroxyphenyl)(2-ethylimidazo[1,2-a]pyridine-3-yl)methanone; (6-Deuterium-2-ethylimidazo[1,2-a]pyridine-3-yl)(3,5-dibromo-4-hydroxyphenyl)methanone; (2-Cyclopropylimidazo[1,2-a]pyridin-3-yl)(3,5-dibromo-4-hydroxyphenyl)methanone; 3-Bromo-5-(2-ethylimidazo[1,2-a]pyridine-3-carbonyl)-2-hydroxybenzonitrile hydrogen chloride; and 5-(2-Ethylimidazo[1,2-a]pyridine-3-carbonyl)-2-hydroxy-3-iodobenzonitrile hydrogen chloride.

The compounds of the present invention can be prepared by the following synthetic methods:

General scheme 1:

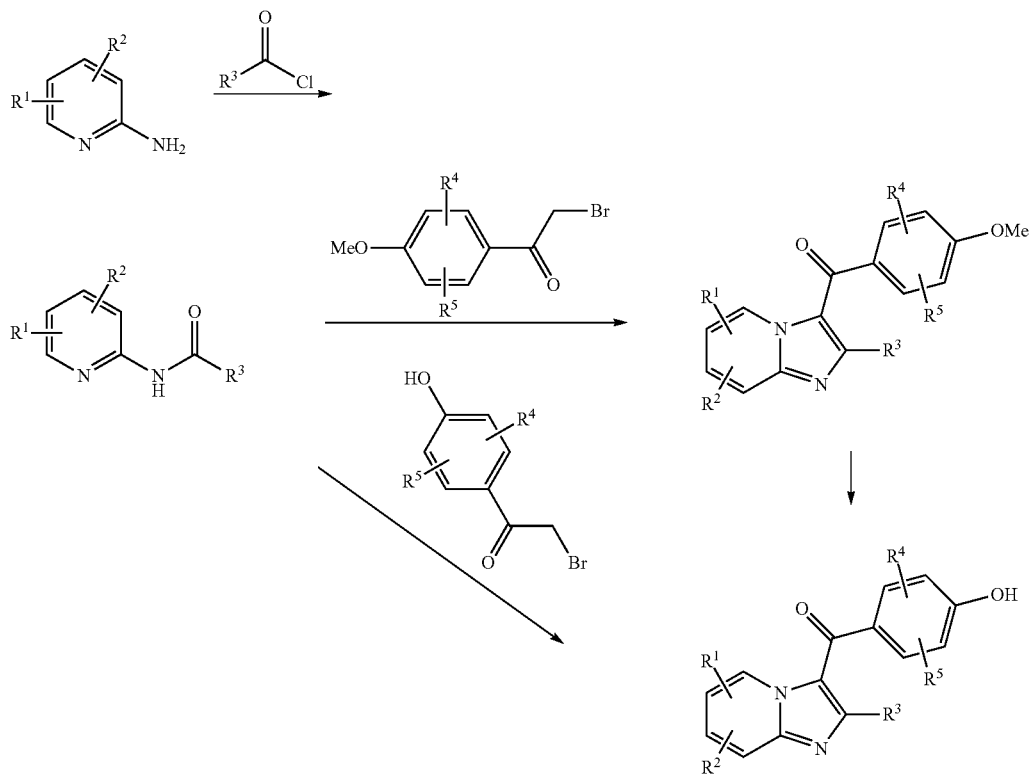

In the general scheme 1, the substituted 2-aminopyridine was reacted with acyl chloride to give the corresponding amide, which was further reacted with substituted 2-bromo-1-phenylethanone to obtain the corresponding (imidazo[1,2-a]pyridin-3-yl)-(phenyl)methanone. The compound may be the final product, or the target product was obtained by demethylation, halogenation and/or other reactions.

General scheme 2:

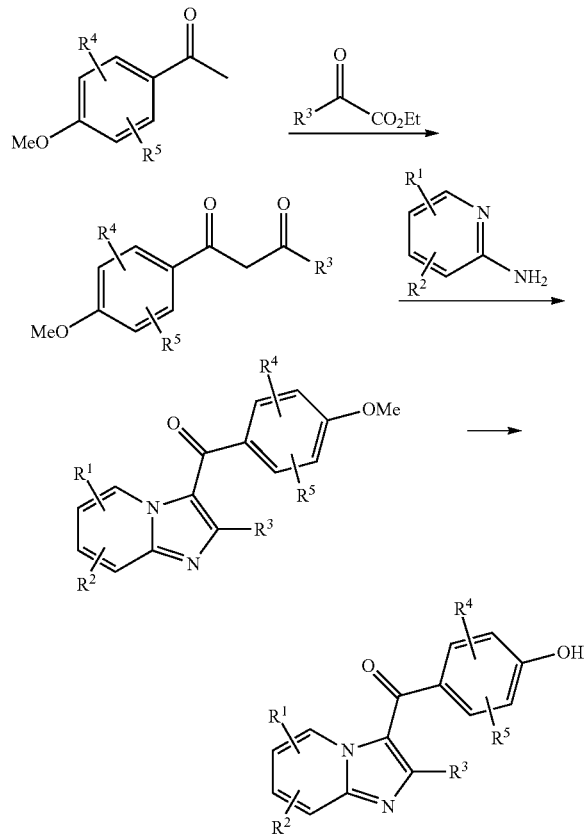

In the general scheme 2, the substituted acetophenone was reacted with the corresponding ester to give 1,3-diketone compound which was reacted with the corresponding 2-aminopyridine to obtain (imidazo[1,2-a]pyridin-3-yl)-(phenyl)methanone. The target compound was afforded by demethylation, halogenation and/or other reactions.

The definition of each group in the synthetic schemes is as described below.

Unless otherwise stated, the following terms used in the claims and instructions have the meanings given below.

"Hydrogen" refers to protium (1H) which is a main stable isotope of hydrogen.

"Deuterium" is a stable isotope of hydrogen and also referred to as heavy hydrogen, and its symbol of element is D.

"Halogen" refers to fluorine atom, chlorine atom, bromine atom or iodine atom.

"Alkyl" is a saturated aliphatic group having 1 to 20 carbon atoms, including a straight-chain group and a branched-chain group (the numerical range (e.g., 1 to 20) mentioned in the present application means that this group (alkyl in this case) may contain one carbon atom, two carbon atoms, three carbon atoms or even twenty carbon atoms). An alkyl containing 1 to 4 carton atoms is called a low-level alkyl. A low-level alkyl without any substituent group is called an unsubstituted low-level alkyl, for example, methyl, ethyl, propyl, 2-propyl, n-butyl, isobutyl, tert-butyl or the like. The alkyl may be substituted or unsubstituted.

"Alkoxy" represents —O— (unsubstituted alkyl) and —O— (unsubstituted cycloalkyl), and further represents —O— (unsubstituted alkyl). Representative examples include but are not limited to methoxy, ethoxy, propoxy, butoxy, cyclopropoxy, cyclobutoxy, cyclopentyloxy, cyclohexyloxy, or the like.

"Alkylthio" represents the —S— (unsubstituted alkyl) and —S— (unsubstituted cycloalkyl) groups, further indicates the —S— (unsubstituted alkyl). Representative examples include but not limited to methionyl, ethylthio, propylthio, butylthio, or cyclopropylthio, cyclobutylthio, cyclopentythio, cyclohexylthio, the like.

"Alkenyl" represents a linear or branched hydrocarbyl group having from 2 to 7 carbon atoms and, in some embodiments, from 2 to 6 carbon atoms or 2 to 4 carbon atoms. Representative examples include for example, ethenyl, propenyl, allyl, and the like.

"Alkynyl" represents a linear monovalent hydrocarbon radical or a branched monovalent hydrocarbon radical having from 2 to 7 carbon atoms and, in some embodiments, from 2 to 6 carbon atoms or 2 to 4 carbon atoms. Representative examples include ethynyl, propynyl, propargyl, and the like.

"Cycloalkyl" represents a single or double ring alkyl group with more than 3 carbon atoms, including but not limited to cyclopropyl, cyclobutyl, cyclohexenyl, and dicycloheptyl groups.

"Cyano" represents the group —CN.

"Pharmaceutically acceptable salts" are salts formed by the compounds of formula (I) with organic acids or inorganic acids, and represent salts maintaining the bioavailability and properties of the parent compounds. These salts include:

(1) salts formed by the compounds with acids, which are obtained by reacting free bases of the parent compounds with inorganic acids or organic acids, wherein the inorganic acids include (but not limited to): for example, hydrochloric acid, hydrobromic acid, nitric acid, phosphoric acid, metaphosphoric acid, sulfuric acid, sulfurous acid, perchloric acid and the like; the organic acids include (but not limited to): for example, acetic acid, propanoic acid, acrylic acid, oxalic acid, (D) or (L) malic acid, fumaric acid, maleic acid, hydroxybenzoic acid, γ-hydroxybutyric acid, methoxybenzoic acid, phthalic acid, methanesulfonic acid, ethanesulfonic acid, 1-naphthalenesulphonic acid, 2-naphthalenesulphonic acid, p-toluenesulfonic acid, salicylic acid, tartaric acid, citric acid, lactic acid, mandelic acid, succinic acid, malonic acid and the like; and (2) salts generated by substituting acidic protons in the parent compounds with metal ions or coordinating the acidic protons in the parent compounds with organic alkalis, wherein the metal ions include, for example, alkali metal ions, alkaline-earth metal ions or aluminum ions; and the organic alkalis include, for example, ethanolamine, diethanolamine, triethanolamine, trometamol, N-methylglucamine and the like.

"Pharmaceutical composition" refers to the mixture of one or more compounds described herein, or their pharmaceutically acceptable salts and prodrugs, together with other chemical components, such as pharmaceutically acceptable carriers and excipients. The purpose of the pharmaceutical composition is to promote the drug delivery of the compound to the organism.

In the following section, unless specifically restricted, compounds (I), which are active ingredients of therapeutic agents, including all their pharmaceutically acceptable salts, should be understood to fall into the scope of this invention. In this specification, they are simply referred to as compounds of formula (I) for convenience.

The invention comprises a pharmaceutical composition, which comprises any compound of the invention, its pharmaceutically acceptable salt or its easily hydrolyzed prodrug ester as an active ingredient, supplemented by pharmaceutically acceptable excipients.

The above compounds of formula (I) in the invention have been confirmed in the following embodiments, they can significantly improve the inhibitory effect on URAT1, significantly increase uric acid excretion in mice, and the toxicity is far lower than that of benzbromoron. Therefore, the compound provided by the present invention has more excellent uric acid excretion effect and higher safety. Based on these properties, a compound or a pharmaceutically acceptable salt thereof can be used in the preparation of uricosuric drug for the treatment of the diseases related to the disorder of uric acid excretion, especially used in the treatment or prevention of hyperuricemia, nephrosis or gout.

SPECIFIC IMPLEMENTATION METHODS

Example 1: Synthesis of (3,5-dibromo-4-hydroxyphenyl)(2-ethylimidazo[1,2-a]-pyridin-3-yl)methanone (4)

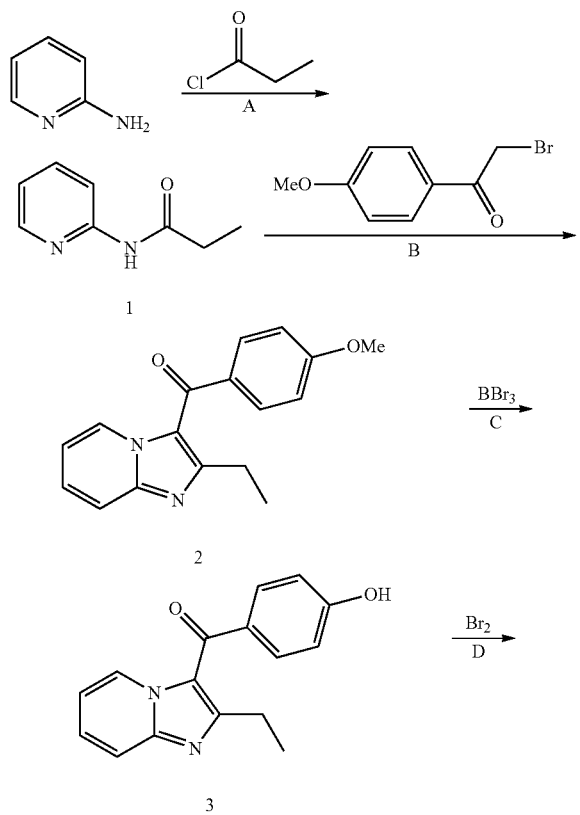

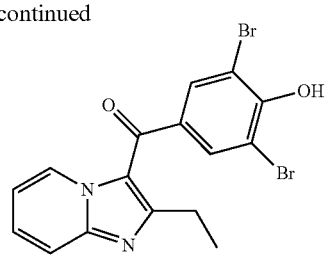

Step A: To a mixture of 2-aminopyridine (2.0 g, 21.3 mmol) and triethylamine (2.58 g, 25.5 mmol) in dichloromethane (20 mL) was added propionyl chloride (2.07 g, 22.4 mmol) dropwise in an ice-water bath. After addition, the reaction mixture was warmed to room temperature and stirred overnight, diluted with water (40 mL), extracted with dichloromethane (40 mL×3). The combined organic layer was washed with brine (30 mL), dried over anhydrous sodium sulfate, concentrated under vacuum. The residue was purified by flash column chromatography on silica gel (eluted with ethyl acetate/petroleum ether=1:15-1:10) to give N-(pyridine-2-yl)propionamide (1) (2.74 g) with 85.6% yield.

Step B: A mixture of compound 1 (300 mg, 2.0 mmol) and 2-bromo-1-(4-methoxyphenyl)-ethanone (460 mg, 2.0 mmol) in toluene (10 mL) was heated under reflux for 48 h. The reaction mixture was cooled to room temperature, diluted with water (30 mL), adjusted to pH 8-9 with saturated potassium carbonate, extracted with dichloromethane (40 mL×3). The combined organic layer was dried over anhydrous sodium sulfate, and concentrated under vacuum. The residue was purified by flash column chromatography on silica gel (eluted with ethyl acetate/petroleum ether=1:30-1:1) to afford (2-ethylimidazo[1,2-a]pyridine-3-yl)(4-methoxyphenyl)methanone (2) (254 mg) with 45.3% yield. $^{1}$H NMR (DMSO-d6, 500 MHz) δ 9.18 (d, J=7.0 Hz, 1H), 7.74-7.69 (m, 3H), 7.58-7.55 (m, 1H), 7.17-7.14 (m, 1H), 7.09 (d, J=8.5 Hz, 2H), 3.87 (s, 3H), 2.45 (q, J=7.5 Hz, 2H), 1.11 (t, J=7.5 Hz, 3H). MS (EI, m/z): 281.1 [M+H]$^{+}$.

Step C: Boron tribromide (0.6 mL, 1.0 M in toluene) was added dropwise into a solution of compound 2 (80 mg, 0.285 mmol) in anhydrous dichloromethane (6 mL) in an ice-water bath. After addition, the reaction mixture was warmed to room temperature, stirred overnight, poured into ice-water (30 mL), adjusted to pH 7-8 with saturated sodium bicarbonate, and extracted with ethyl acetate (40 mL×2). The combined organic layer was dried over anhydrous sodium sulfate, filtered and evaporated under vacuum. The residue was purified by flash column chromatography on silica gel (eluted with ethyl acetate/petroleum ether=1:20-1:1) to afford (2-ethylimidazo[1,2-a]-pyridine-3-yl)(4-hydroxyphenyl)methanone (3) (67 mg) with 88.3% yield. $^{1}$H NMR (DMSO-d6, 300 MHz) δ 10.29 (s, 1H), 9.11 (d, J=6.6 Hz, 1H), 7.71 (d, J=9.0 Hz, 1H), 7.62-7.51 (m, 3H), 7.15-7.11 (m, 1H), 6.90 (d, J=8.4 Hz, 2H), 2.45 (q, J=7.5 Hz, 2H), 1.12 (t, J=7.5 Hz, 3H). MS (EI, m/z): 267.2 [M+H]$^{+}$.

Step D: To a mixture of compound 3 (67 mg, 0.252 mmol) and sodium acetate (62 mg, 0.755 mmol) in acetic acid (5 mL) was added bromine (90 mg, 0.563 mmol) in acetic acid (1 mL). The resulting mixture was stirred at room temperature for 3 h, quenched by addition of saturated aqueous sodium bisulfate, and concentrated under vacuum. To the residue was added water (30 mL), and the mixture was adjusted to pH 7-8 with saturated sodium bicarbonate and extracted with ethyl acetate (40 mL×2). The combined organic layer was dried over anhydrous sodium sulfate and concentrated under vacuum. The residue was purified by flash column chromatography on silica gel (eluted with ethyl acetate/petroleum ether=1:10-1:1) to afford (3,5-dibromo-4-hydroxyphenyl)(2-ethylimidazo[1,2-a]pyridine-3-yl)methanone (4) (48 mg) with 44.9% yield. $^1$H NMR (DMSO-d6, 300 MHz) δ 9.19 (d, J=6.9 Hz, 1H), 7.87 (s, 2H), 7.75 (d, J=9.0 Hz, 1H), 7.63-7.58 (m, 1H), 7.22-7.17 (m, 1H), 2.44 (q, J=7.5 Hz, 2H), 1.17 (t, J=7.5 Hz, 3H). MS (EI, m/z): 422.9 [M+H]$^+$.

Example 2: Synthesis of (2-ethylimidazo[1,2-a]pyridine-3-yl)(4-hydroxy-3,5-diiodophenyl)methanone (5)

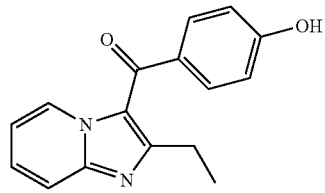

3

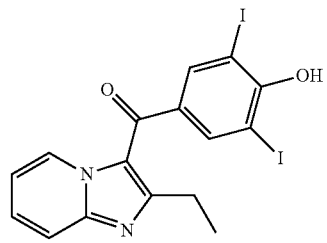

5

A mixture of compound 3 (556 mg, 2.09 mmol), sodium acetate (367 mg, 4.58 mmol) and iodine (1.17 g, 4.61 mmol) in methanol (20 mL) was stirred under reflux for 1 h. Then a solution of sodium hydroxide (151 mg, 3.78 mmol) in water (20 mL) was added. The reaction mixture was stirred under reflux for 1 h and cooled to room temperature. Saturated aqueous sodium bisulfate (20 mL) was added. The precipitates formed were collected by filtration, washed with water, and dried. The crude product was crystallized from petroleum ether/ethyl acetate to give (2-ethylimidazo[1,2-a]-pyridine-3-yl)(4-hydroxy-3,5-diiodophenyl)methanone (5) (924 mg) with 85.3% yield. $^1$H NMR (DMSO-d6, 300 MHz) δ 9.17 (d, J=6.9 Hz, 1H), 8.05 (s, 2H), 7.75 (d, J=9.0 Hz, 1H), 7.64-7.58 (m, 1H), 7.22-7.17 (m, 1H), 2.45 (q, J=7.5 Hz, 2H), 1.17 (t, J=7.5 Hz, 3H). MS (EI, m/z): 518.8 [M+H]$^+$.

Example 3: Synthesis of (3-chloro-4-hydroxyphenyl)(2-ethylimidazo[1,2-a]pyridin-3-yl)methanone (8) and (3-chloro-4-hydroxy-5-iodophenyl)(2-ethyl-imidazo[1,2-a]-pyridin-3-yl)methanone (9)

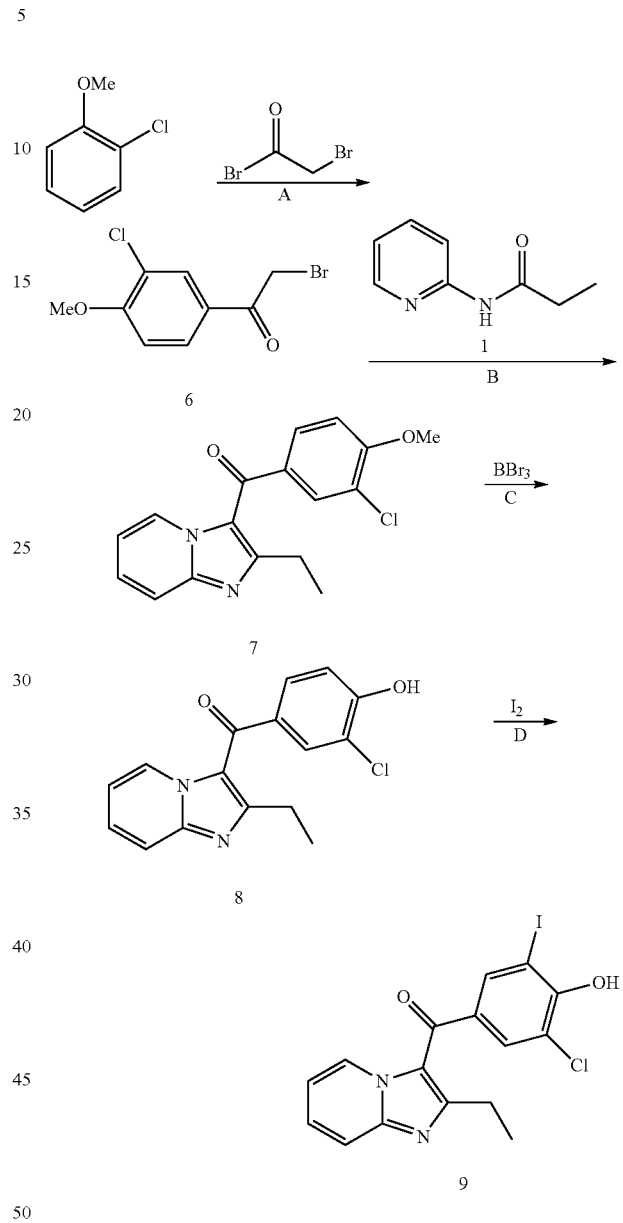

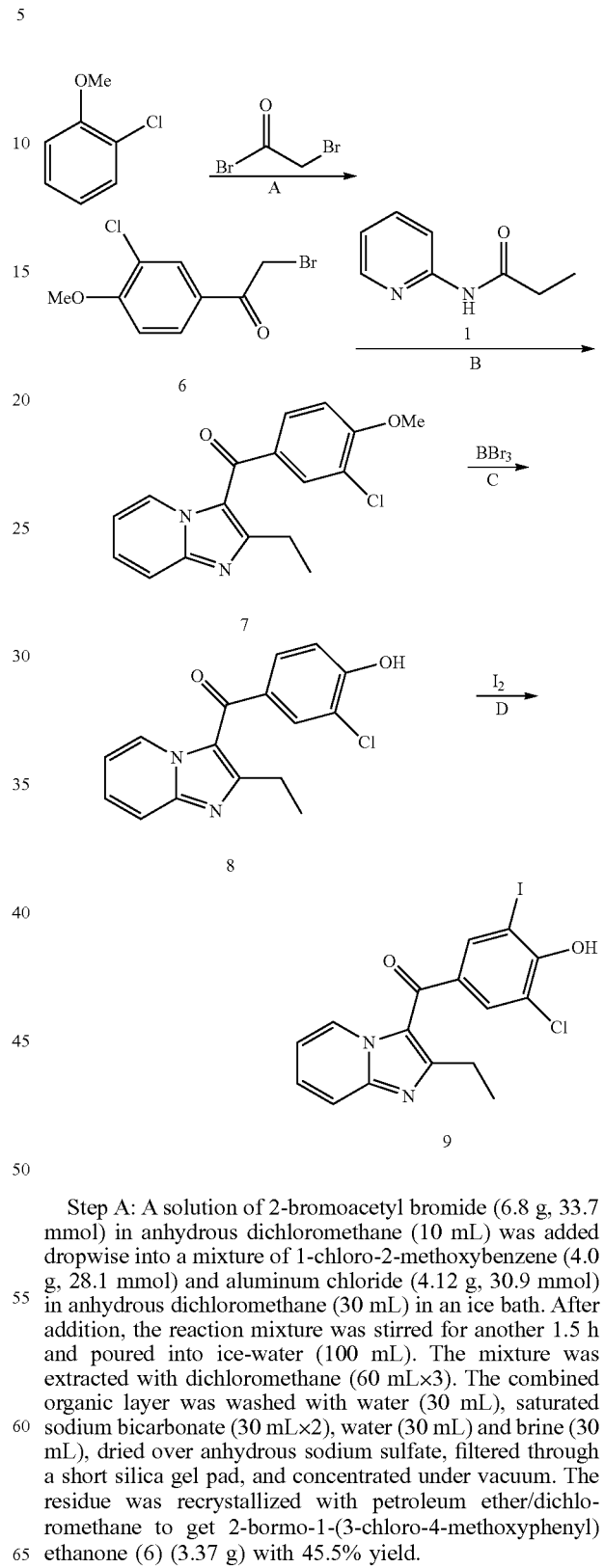

Step A: A solution of 2-bromoacetyl bromide (6.8 g, 33.7 mmol) in anhydrous dichloromethane (10 mL) was added dropwise into a mixture of 1-chloro-2-methoxybenzene (4.0 g, 28.1 mmol) and aluminum chloride (4.12 g, 30.9 mmol) in anhydrous dichloromethane (30 mL) in an ice bath. After addition, the reaction mixture was stirred for another 1.5 h and poured into ice-water (100 mL). The mixture was extracted with dichloromethane (60 mL×3). The combined organic layer was washed with water (30 mL), saturated sodium bicarbonate (30 mL×2), water (30 mL) and brine (30 mL), dried over anhydrous sodium sulfate, filtered through a short silica gel pad, and concentrated under vacuum. The residue was recrystallized with petroleum ether/dichloromethane to get 2-bormo-1-(3-chloro-4-methoxyphenyl)ethanone (6) (3.37 g) with 45.5% yield.

Step B: A mixture of compound 1 (780 mg, 5.23 mmol) and compound 6 (1.37 g, 5.20 mmol) in toluene (20 mL) was stirred under reflux for 24 h and cooled to room temperature. After addition of water (50 mL), the reaction mixture was adjusted to pH 8-9 with saturated potassium carbonate and extracted with dichloromethane (60 mL×3). The organic layer was dried over anhydrous sodium sulfate, filtered, and concentrated under vacuum. The residue was purified by flash column chromatography on silica gel (eluted with ethyl acetate/petroleum ether=1:20-1:5) to afford (3-chloro-4-methoxyphenyl)(2-ethylimidazo[1,2-a]pyridine-3-yl)methanone (7) (510 mg) with 31.2% yield.

Step C: Boron tribromide (3.2 mL, 1.0 M in toluene) was added dropwise into a mixture of compound 7 (500 mg, 1.57 mmol) in anhydrous dichloromethane (15 mL) in an ice-water bath. The reaction mixture was stirred at room temperature overnight, poured into ice-water (40 mL), adjusted to pH 7-8 with saturated sodium bicarbonate, and extracted with ethyl acetate (40 mL×2). The organic layer was dried over anhydrous sodium sulfate, filtered, and concentrated under vacuum. The residue was purified by flash column chromatography on silica gel (eluted with ethyl acetate/petroleum ether=1:5-3:1) to afford (3-chloro-4-hydroxyphenyl)(2-ethylimidazo[1,2-a]-pyridine-3-yl)methanone (8) (380 mg) with 79.5% yield. MS (EI, m/z): 301.7 [M+H]$^+$.

Step D: A mixture of compound 8 (378 mg, 1.26 mmol), sodium acetate (114 mg, 1.39 mmol) and iodine (351 mg, 1.38 mmol) in methanol (30 mL) was stirred under reflux for 1 h. After adding a solution of sodium hydroxide (45 mg, 1.13 mmol) into water (13 mL), the reaction mixture was stirred under reflux for 1 h and cooled to room temperature. Saturated aqueous sodium bisulfate (30 mL) was added. The precipitates were collected by filtration, washed with water, and dried. The crude product was recrystallized with petroleum ether/ethyl acetate to afford (3-chloro-4-hydroxy-5-iodophenyl)(2-ethylimidazo[1,2-a]pyridine-3-yl)methanone (9) (430 mg) with 85.3% yield. $^1$H NMR (DMSO-d6, 500 MHz) δ 9.04 (d, J=7.0 Hz, 1H), 7.95 (d, J=1.5 Hz, 1H), 7.71-7.68 (m, 2H), 7.54-7.51 (m, 1H), 7.13-7.10 (m, 1H), 2.49-2.47 (m, 2H), 1.18 (t, J=7.5 Hz, 3H). MS (EI, m/z): 426.9 [M+H]$^+$.

Example 4: Synthesis of 3-chloro-5-(2-ethylimidazo[1,2-a]pyridine-3-carbonyl)-2-hydroxybenzonitrile (10)

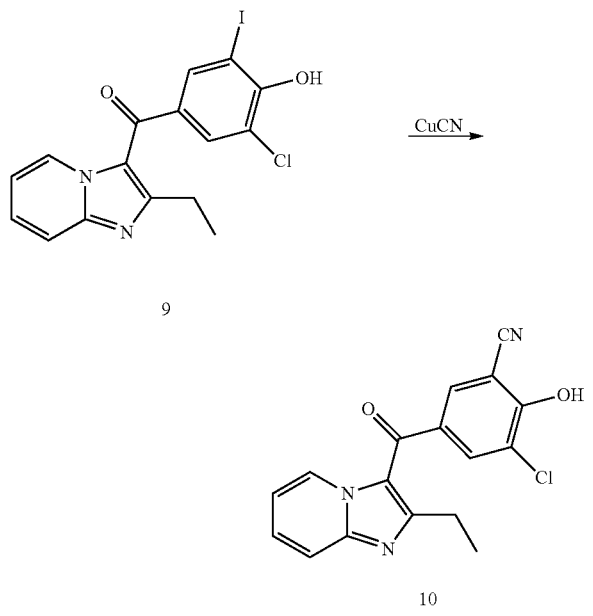

A mixture of compound 9 (393 mg, 0.921 mmol) and cuprous cyanide (124 mg, 1.38 mmol) in DMF (5 mL) was stirred at 130° C. overnight, cooled to room temperature, diluted with water (30 mL), and extracted with ethyl acetate (30 mL×3). The combined organic layer was washed with water (20 mL×2) and brine (10 mL), dried over anhydrous sodium sulfate, filtered, and concentrated under vacuum. The residue was purified by flash column chromatography on silica gel (eluted with ethyl acetate/petroleum ether=2:1-5:1) to afford 3-chloro-5-(2-ethylimidazo[1,2-a]pyridine-3-carbonyl)-2-hydroxybenzonitrile (10). $^1$H NMR (DMSO-d6, 300 MHz) δ 9.11 (d, J=6.3 Hz, 1H), 7.94-7.90 (m, 2H), 7.80-7.77 (m, 1H), 7.68-7.63 (m, 1H), 7.26-7.21 (m, 1H), 2.50-2.48 (m, 2H), 1.17 (t, J=7.2 Hz, 3H). MS (EI, m/z): 324.0 [M−H]$^-$.

Example 5: Synthesis of (3-bromo-4-hydroxy-5-iodophenyl)(2-ethylimidazo[1,2-a]-pyridine-3-yl)methanone (11)

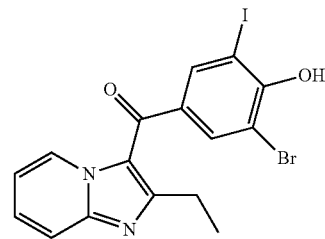

Compound 11 was prepared according to the procedure of example 3 by using 1-bromo-2-methoxybenzene in step A as an alternative reagent. $^1$H NMR (DMSO-d6, 300 MHz) δ 9.16 (d, J=6.9 Hz, 1H), 8.03 (d, J=1.8 Hz, 1H), 7.87 (d, J=1.8 Hz, 1H), 7.74 (d, J=8.7 Hz, 1H), 7.62-7.56 (m, 1H), 7.20-7.16 (m, 1H), 2.43 (t, J=7.5 Hz, 2H), 1.18 (t, J=7.5 Hz, 3H). MS (EI, m/z): 470.9 [M+H]$^+$.

Example 6: Synthesis of (2-ethylimidazo[1,2-a]pyridine-3-yl)(4-hydroxy-3-iodo-5-methylphenyl)methanone (12)

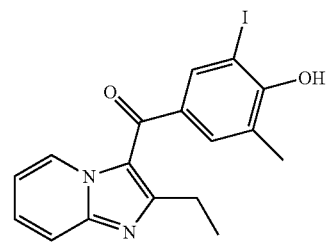

Compound 12 was prepared according to the procedure of example 3 by using 1-methoxy-2-methylbenzene in step A as an alternative reagent. $^1$H NMR (DMSO-d6, 300 MHz) δ 9.91 (s, 1H), 9.14 (dd, J=0.9, 6.9 Hz, 1H), 7.88 (s, 1H), 7.74-7.71 (m, 1H), 7.59-7.51 (m, 2H), 7.18-7.13 (m, 1H), 2.44 (t, J=7.5 Hz, 2H), 2.30 (s, 3H), 1.17 (t, J=7.5 Hz, 3H). MS (EI, m/z): 406.9 [M+H]$^+$.

Example 7: Synthesis of (2-ethylimidazo[1,2-a]pyridine-3-yl)(4-hydroxy-3-iodophenyl)-methanone (13)

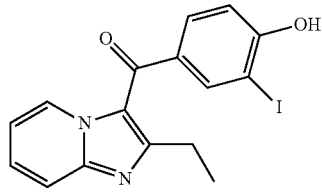

Compound 13 was prepared according to the procedures of steps A, B and C in example 3 by using 1-iodo-2-methoxybenzene as an alternative reagent. $^1$H NMR (DMSO-d6, 500 MHz) δ 11.16 (s, 1H), 9.13 (d, J=7.0 Hz, 1H), 8.02 (d, J=1.5 Hz, 1H), 7.71 (d, J=8.5 Hz, 1H), 7.61 (dd, J=2.0, 8.0 Hz, 1H), 7.57-7.54 (m, 1H), 7.16-7.13 (m, 1H), 7.01 (d, J=8.5 Hz, 1H), 2.45 (q, J=7.5 Hz, 2H), 1.15 (t, J=7.5 Hz, 3H). MS (EI, m/z): 392.9 [M+H]$^+$.

Example 8: Synthesis of 5-(2-ethylimidazo[1,2-a]pyridine-3-carbonyl)-2-hydroxybenzonitrile (14)

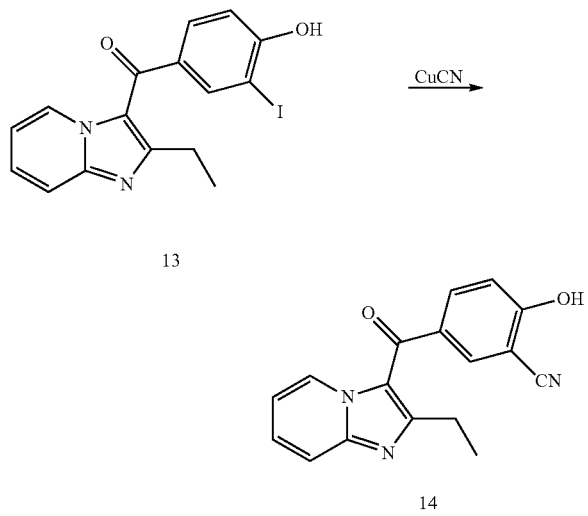

Using compound 13 as the starting material, compound 14 was prepared according to the procedure of example 4. $^1$H NMR (DMSO-d6, 500 MHz) δ 11.91 (s, 1H), 9.19 (d, J=6.5 Hz, 1H), 7.98 (d, J=2.0 Hz, 1H), 7.85 (dd, J=2.0, 8.5 Hz, 1H), 7.74 (d, J=9.0 Hz, 1H), 7.61-7.57 (m, 1H), 7.19-7.15 (m, 2H), 2.43 (q, J=7.5 Hz, 2H), 1.13 (t, J=7.5 Hz, 3H). MS (EI, m/z): 292.0 [M+H]$^+$.

Example 9: Synthesis of (3-bromo-5-chloro-4-hydroxyphenyl)(2-ethyl-6-fluoroimidazo[1,2-a]pyridine-3-yl)methanone (18)

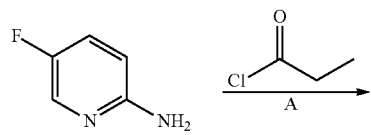

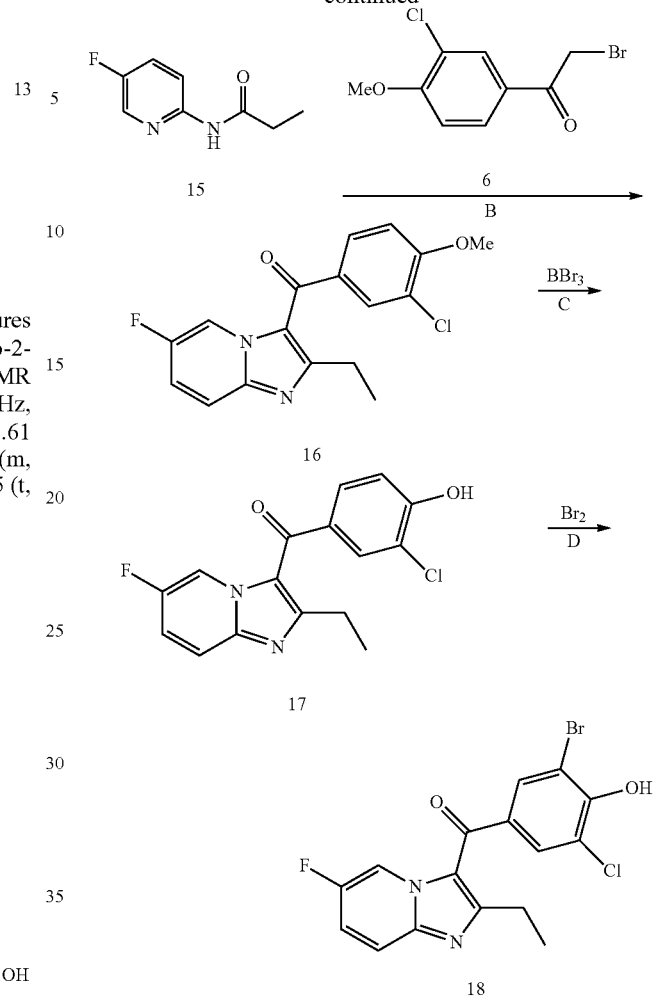

Step A: To a mixture of 2-amino-5-fluoropyridine (2.5 g, 22.3 mmol) and triethylamine (2.71 g, 26.8 mmol) in anhydrous dichloromethane (25 mL) was added propionyl chloride (2.17 g, 23.5 mmol) dropwise in an ice-water bath. After addition, the reaction mixture was stirred at room temperature overnight, quenched with water (40 mL), and extracted with dichloromethane (40 mL×3). The combined organic layer was washed with brine (30 mL), dried over anhydrous sodium sulfate, filtered, and concentrated under vacuum. The residue was purified by flash column chromatography on silica gel (eluted with ethyl acetate/petroleum ether=1:5) to afford N-(5-fluoropyridine-2-yl)propionamide (15) (3.04 g) with 81.1% yield.

Step B: A mixture of compound 15 (960 mg, 5.71 mmol) and compound 6 (1.5 g, 5.69 mmol) in toluene (30 mL) was stirred under reflux overnight, cooled to room temperature, diluted with water (30 mL), adjusted to pH 8-9 with saturated potassium carbonate, and extracted with dichloromethane (40 mL×3). The combined organic layer was washed with water, dried over anhydrous sodium sulfate, and concentrated under vacuum. The residue was purified by flash column chromatography on silica gel (eluted with ethyl acetate/petroleum ether=1:30-1:1) to afford (3-chloro-4-methoxyphenyl)(2-ethylimidazo[1,2-a]pyridine-3-yl)methanone (16) (270 mg) with 14.3% yield.

Step C: A 1.0 M solution of boron tribromide in toluene (2.4 mL) was added dropwise into a mixture of compound 16 (262 mg, 0.787 mmol) in anhydrous dichloromethane (10 mL) in an ice-water bath. The reaction mixture was stirred at room temperature for 6 h, diluted with ice-water (30 mL), adjusted to pH 7-8 with saturated sodium bicarbonate, and extracted with ethyl acetate (40 mL×3). The combined organic layer was dried over anhydrous sodium sulfate and concentrated under vacuum. The residue was purified by flash column chromatography on silica gel (eluted with ethyl acetate/petroleum ether=1:6-1:4) to afford (3-chloro-4-hydroxyphenyl)(2-ethyl-6-fluoroimidazo[1,2-a]pyridin-3-yl)methanone (17) (90 mg) with 35.9% yield. MS (EI, m/z): 339.7 [M+H]$^+$.

Step D: To a mixture of compound 17 (41 mg, 0.129 mmol) and sodium acetate (26 mg, 0.317 mmol) in acetic acid (5 mL) was added bromine (25 mg, 0.156 mmol) in acetic acid (1 mL). The resulting mixture was stirred at room temperature for 1.5 h, quenched by saturated aqueous sodium bisulfate, and then concentrated under vacuum. To the residue was added water (20 mL), and the mixture was adjusted to pH 7-8 with saturated sodium bicarbonate and extracted with ethyl acetate (30 mL×3). The combined organic layer was dried over anhydrous sodium sulfate and concentrated under vacuum. The residue was purified by flash column chromatography on silica gel (eluted with ethyl acetate/petroleum ether=1:6-1:3) to afford (3-bromo-5-chloro-4-hydroxyphenyl)-(2-ethyl-6-fluoroimidazo[1,2-a]pyridine-3-yl)methanone (18). $^1$H NMR (DMSO-d6, 500 MHz) δ 11.06 (s, 1H), 9.22-9.21 (m, 1H), 7.86-7.83 (m, 2H), 7.76-7.70 (m, 2H), 2.43 (q, J=7.5 Hz, 2H), 1.16 (t, J=7.5 Hz, 3H). MS (EI, m/z): 398.9 [M+H]$^+$.

Example 10: Synthesis of (3-chloro-4-hydroxy-5-iodophenyl)(2-ethyl-6-fluoroimidazo[1,2-a]pyridine-3-yl)methanone (19)

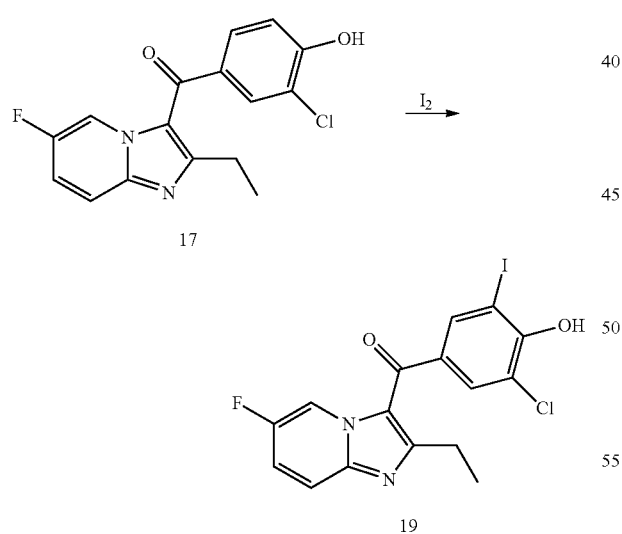

A mixture of compound 17 (41 mg, 0.129 mmol), sodium acetate (12 mg, 0.146 mmol) and iodine (36 mg, 0.142 mmol) in methanol (10 mL) was stirred under reflux for 1 h, and then a solution of sodium hydroxide (5 mg, 0.125 mmol) in water (3 mL) was added. The reaction mixture was stirred under reflux for 1 h, cooled to room temperature, and added saturated aqueous sodium bisulfate (10 mL). The precipitates formed were collected by filtration, washed with water and dried. The crude product was crystallized with petroleum ether/ethyl acetate to get (3-chloro-4-hydroxy-5-iodophenyl)(2-ethyl-6-fluoroimidazo[1,2-a]pyridin-3-yl)methanone (19). $^1$H NMR (DMSO-d6, 500 MHz) δ 9.13 (s, 1H), 7.97 (d, J=2.0 Hz, 1H), 7.83-7.80 (m, 1H), 7.71 (d, J=2.0 Hz, 1H), 7.69-7.65 (m, 1H), 2.46 (q, J=7.5 Hz, 2H), 1.17 (t, J=7.5 Hz, 3H). MS (EI, m/z): 444.9 [M+H]$^+$.

Example 11: Synthesis of 5-(2-ethylimidazo[1,2-a]pyridine-3-carbonyl)-2-hydroxy-3-methylbenzonitrile (24)

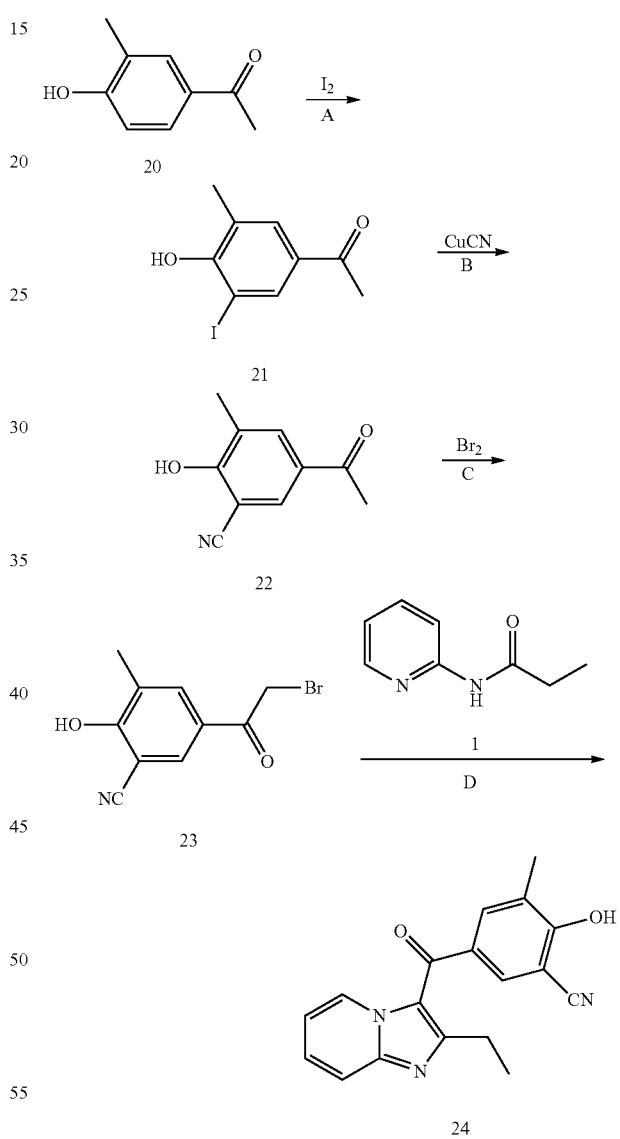

Step A: A mixture of 1-(4-hydroxy-3-methylphenyl)ethanone (4.95 g, 33.0 mmol), sodium acetate (2.98 g, 36.3 mmol) and iodine (9.21 g, 36.3 mmol) in methanol (80 mL) was stirred under reflux for 1 h, and then a solution of sodium hydroxide (1.19 g, 29.7 mmol) in water (55 mL) was added. The reaction mixture was stirred under reflux for 1 h and evaporated to about half of the volume under vacuum. The precipitates formed were collected by filtration. The cake was dissolved into ethyl acetate (200 mL), and the solution was washed with saturated aqueous sodium bisulfate (40 mL) and brine (40 mL), dried over anhydrous sodium sulfate and concentrated to give 1-(4-hydroxy-3-iodo-5-methylphenyl)ethanone (21) (7.91 g) with 86.8% yield.

Step B: A mixture of compound 21 (3.90 g, 14.1 mmol) and cuprous cyanide (1.90 g, 21.2 mmol) in DMF (25 mL) was stirred at 130° C. overnight. The reaction mixture was cooled to room temperature and filtered through a celite pad. To the filtrate was added water (100 mL). The mixture was extracted with ethyl acetate (50 mL×3). The combined organic layer was washed with water (30 mL×2) and brine (30 mL), dried over anhydrous sodium sulfate, and concentrated under vacuum. The residue was purified by flash column chromatography on silica gel (eluted with ethyl acetate/petroleum ether=1:15-1:3) to afford 5-acetyl-2-hydroxy-3-methyl-benzonitrile (22) (2.07 g) with 83.8% yield.

Step C: To a solution of compound 22 (500 mg, 2.85 mmol) in methanol (10 mL) was added bromine (548 mg, 3.43 mmol) in methanol (4 mL), and the reaction mixture was stirred at room temperature for 6 h. After addition of water (50 mL), the resulting mixture was extracted with ethyl acetate (40 mL×3). The combined organic layer was washed with brine (20 mL), dried over anhydrous sodium sulfate, and concentrated under vacuum to afford 5-(2-bromoacetyl)-2-hydroxy-3-methylbenzonitrile (23) (800 mg). The crude product 23 was used directly in the next step without further purification.

Step D: A mixture of crude compound 23 (800 mg) and compound 1 (600 mg, 3.99 mmol) in toluene (15 mL) was stirred under reflux overnight and cooled to room temperature. To the reaction mixture was added methanol (15 mL) and potassium carbonate (1.10 g, 8.0 mmol). The resulting mixture was stirred at room temperature for 30 minutes, diluted with water (40 mL), and extracted with ethyl acetate (50 mL×3). The organic layer was dried over anhydrous sodium sulfate and concentrated under vacuum. The residue was purified by flash column chromatography on silica gel (eluted with ethyl acetate/petroleum ether=1:30-1:1) to afford 5-(2-ethylimidazo[1,2-a]pyridine-3-carbonyl)-2-hydroxy-3-methylbenzonitrile (24). $^1$H NMR (DMSO-d6, 300 MHz) δ 10.99 (s, 1H), 9.15 (d, J=6.9 Hz, 1H), 7.79 (s, 1H), 7.74-7.72 (m, 2H), 7.60-7.55 (m, 1H), 7.19-7.14 (m, 1H), 2.43 (q, J=7.5 Hz, 2H), 2.26 (s, 3H), 1.14 (t, J=7.5 Hz, 3H). MS (EI, m/z): 306.1 [M+H]$^+$.

Example 12: Synthesis of (2-thylimidazo[1,2-a]pyridine-3-yl)(4-hydroxy-3-(trifluoro-methyl)phenyl)methanone (28) and (3-bromo-4-hydroxy-5-(trifluoromethyl)phenyl)-(2-ethylimidazo[1,2-a]pyridine-3-yl)methanone (29)

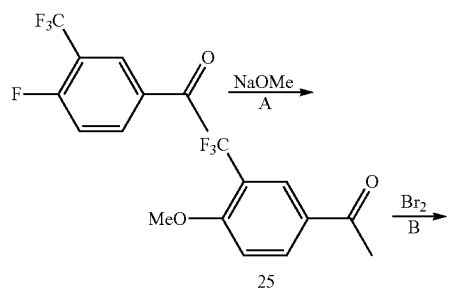

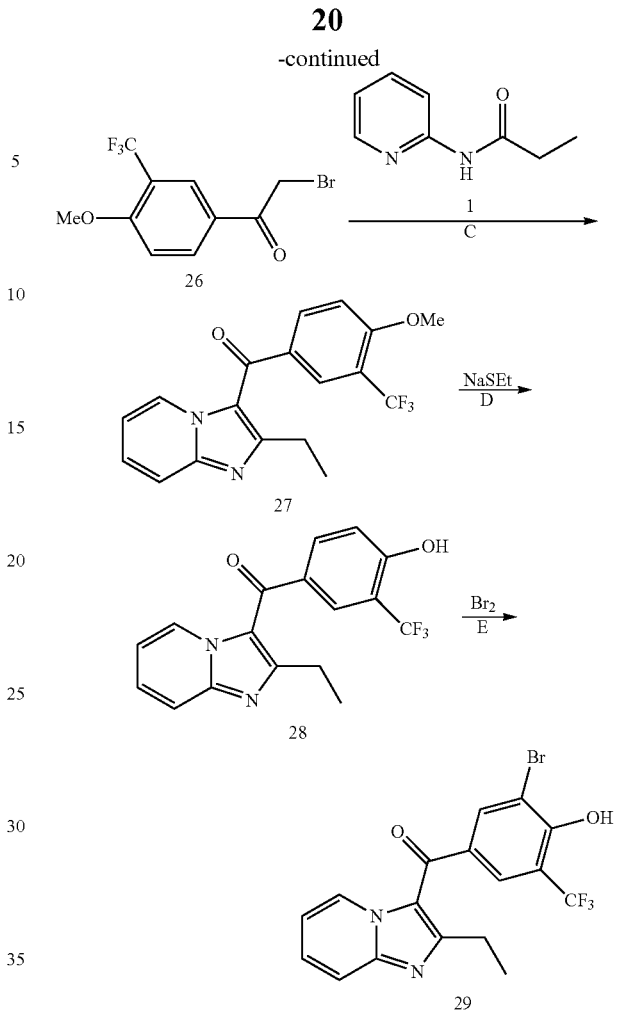

Step A: A mixture of 1-(4-fluoro-3-(trifluoromethyl)phenyl)ethanone (1.0 g, 4.85 mmol) and sodium methoxide (288 mg, 5.33 mmol) in DMF (5 mL) was stirred for 2 h in an ice-water bath and then at room temperature overnight. The reaction mixture was diluted with water (30 mL) and extracted with ethyl acetate (30 mL×3). The combined organic layer was washed with brine (20 mL), dried over anhydrous sodium sulfate, and concentrated under vacuum. The residue was purified by flash column chromatography on silica gel (eluted with ethyl acetate/petroleum ether=1:40) to get 1-(4-methoxy-3-(trifluoromethyl)phenyl)ethanone (25) (950 mg) with 89.8% yield.

Steps B and C were followed the methods used in steps C and D of example 11.

Step D: Sodium hydride (60% in mineral oil, 69 mg, 1.73 mmol) was added portionwise to a solution of ethanethiol (107 mg, 1.73 mmol) in DMF (5 mL), and the mixture was stirred for about 5 minutes at room temperature. A solution of compound 27 (200 mg, 0.574 mmol) in DMF (3 mL) was added into the above mixture. The reaction mixture was stirred at 120° C. for 2 h, cooled to room temperature, and diluted with water (40 mL). The mixture was adjusted to pH 8-9 with 2 M hydrochloric acid and extracted with ethyl acetate (40 mL×3). The combined organic layer was washed with water (30 mL) and brine (20 mL), dried over anhydrous sodium sulfate, and concentrated under vacuum. The residue was purified by flash column chromatography on silica gel (eluted with ethyl acetate/petroleum ether=1:1) to give (2-ethylimidazo[1,2-a]pyridine-3-yl)-(4-hydroxy-3-(trifluoromethyl)phenyl)methanone (28) (120 mg) with 62.6% yield. $^1$H NMR (DMSO-d6, 300 MHz) δ 11.55 (s, 1H), 9.17 (d, J=6.9 Hz, 1H), 7.86 (d, J=6.0 Hz, 2H), 7.75 (d, J=9.0 Hz, 1H), 7.63-7.57 (m, 1H), 7.21-7.16 (m, 1H), 2.43 (q, J=7.5 Hz, 2H), 1.15 (t, J=7.5 Hz, 3H). MS (EI, m/z): 335.1 [M+H]$^+$.

Step E: To a mixture of compound 28 (96 mg, 0.287 mmol) and sodium acetate (59 mg, 0.719 mmol) in acetic acid (5 mL) was added bromine (55 mg, 0.719 mmol) in acetic acid (1 mL). The resulting mixture was stirred at room temperature for 1.5 h, quenched by addition of saturated aqueous sodium bisulfate, concentrated under vacuum, and then diluted with water (20 mL). The mixture was adjusted to pH 7-8 with saturated sodium bicarbonate, extracted with ethyl acetate (40 mL×2), dried over anhydrous sodium sulfate, filtered, and concentrated under vacuum. The residue was purified by flash column chromatography on silica gel (eluted with ethyl acetate/petroleum ether=1:5-3:2) to afford (3,5-dibromo-4-hydroxyphenyl)(2-ethylimidazo[1,2-a]pyridine-3-yl)-methanone (29)(85 mg) with 71.9% yield. $^1$H NMR (DMSO-d6, 500 MHz) δ 9.19 (d, J=6.5 Hz, 1H), 8.15 (s, 1H), 7.88 (s, 1H), 7.77 (d, J=9.0 Hz, 1H), 7.66-7.62 (m, 1H), 7.24-7.21 (m, 1H), 2.41 (q, J=7.5 Hz, 2H), 1.16 (t, J=7.5 Hz, 3H). MS (EI, m/z): 413.0 [M+H]$^+$.

Example 13: Synthesis of (3,5-dibromo-4-hydroxyphenyl)(2-ethyl-6-methylimidazo[1,2-a]pyridine-3-yl)methanone (30)

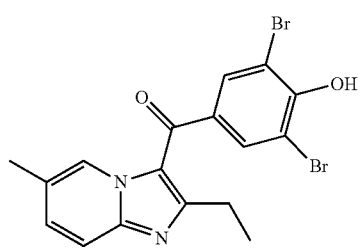

Compound 30 was prepared according to the procedure of example 1 by using 5-methylpyridin-2-amine as an alternative reagent in step A. $^1$H NMR (DMSO-d6, 500 MHz) δ 9.04 (s, 1H), 7.87 (s, 2H), 7.69 (d, J=9.0 Hz, 1H), 7.52 (d, J=9.0 Hz, 1H), 2.42-2.38 (m, 5H), 1.15 (t, J=7.5 Hz, 3H). MS (EI, m/z): 436.9 [M−H]$^-$.

Example 14: Synthesis of (3,5-dibromo-4-hydroxyphenyl)(2-ethyl-6-methoxyimidazo[1,2-a]pyridine-3-yl)methanone (33)

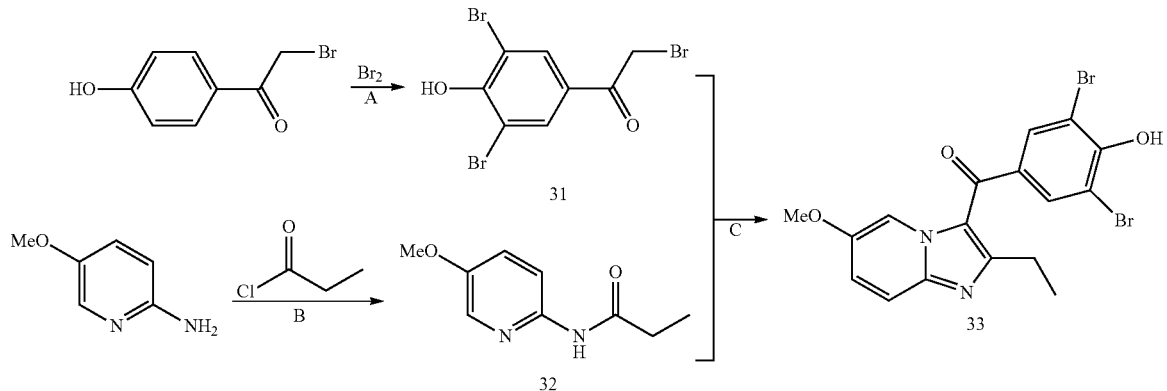

Step A: To a mixture of 2-bromo-1-(4-hydroxyphenyl)ethanone (639 mg, 2.98 mmol) and sodium acetate (740 mg, 9.02 mmol) in acetic acid (10 mL) was added bromine (960 mg, 6.0 mmol) in acetic acid (5 mL), and the resulting mixture was stirred at room temperature for 10 minutes. After addition of water (40 mL), the precipitates formed were collected by filtration, washed with water, and dried to give 2-bromo-1-(3,5-dibromo-4-hydroxyphenyl)ethanone (31) (890 mg) with 80.1% yield.

Step B: To a mixture of 5-methoxypyridin-2-amine (1.0 g, 8.05 mmol) and triethylamine (981 mg, 9.69 mmol) in dichloromethane (8 mL) was added propionyl chloride (777 mg, 8.4 mmol) dropwise in an ice-water bath. After addition, the reaction mixture was warmed to room temperature and stirred overnight. To the reaction mixture was added water (40 mL), and the mixture was extracted with dichloromethane (30 mL×3). The combined organic layer was washed with brine (30 mL), dried over anhydrous sodium sulfate, and concentrated under vacuum. The residue was purified by flash column chromatography on silica gel (eluted with ethyl acetate/petroleum ether=1:30-1:8). The product was recyrstallized with petroleum ether to afford N-(5-methoxypyridine-2-yl)-propionamide (32) (349 mg) with 21.4% yield.

Step C: A mixture of compound 31 (790 mg, 2.12 mmol) and compound 32 (340 mg, 1.89 mmol) in toluene (20 mL) was stirred under reflux for 48 h and cooled to room temperature. To the mixture was added water (50 mL), and the resulting mixture was adjusted to pH 8-9 with saturated potassium carbonate and extracted with dichloromethane (50 mL×3). The combined organic layer was dried over anhydrous sodium sulfate and concentrated under vacuum. The residue was purified by flash column chromatography on silica gel (eluted with ethyl acetate/petroleum ether=1:10-2:5) to afford (3,5-dibromo-4-hydroxyphenyl) (2-ethyl-6-methoxyimidazo[1,2-a]pyridine-3-yl)methanone (33) (87 mg) with 10.1% yield. $^1$H NMR (DMSO-d6, 500 MHz) δ 8.71 (s, 1H), 7.79 (s, 2H), 7.64 (d, J=10.0 Hz, 1H), 7.34 (d, J=10.0 Hz, 1H), 3.81 (s, 3H), 2.45 (q, J=7.5 Hz, 2H), 1.16 (t, J=7.5 Hz, 3H). MS (EI, m/z): 452.9 [M−H]$^-$.

Example 15: Synthesis of 3-bromo-5-(2-ethylimidazo[1,2-a]pyridine-3-carbonyl)-2-hydroxybenzonitrile (38)

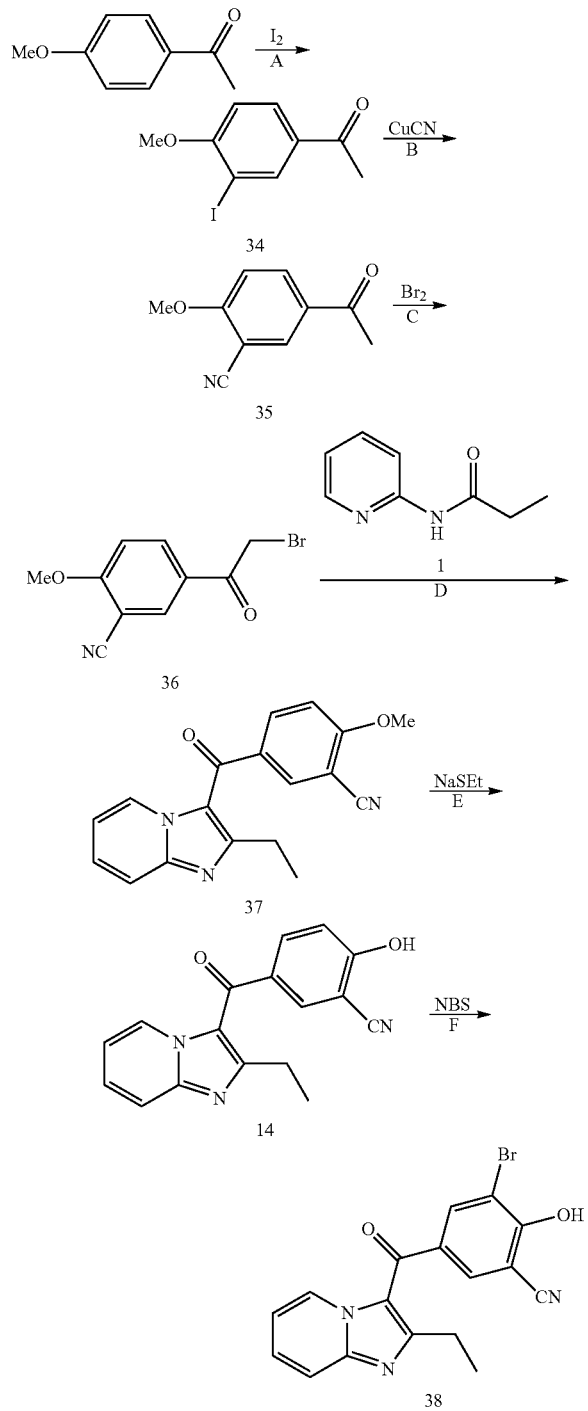

Step A: 1-(4-Methoxyphenyl)ethanone (44 g, 293 mmol) was added into a mixture of 1-chloromethyl-4-fluoro-1,4-diazoniabicyclo[2.2.2]ocatane bis(tetrafluoroborate) (104 g, 294 mmol) and iodine (38.6 g, 152 mmol) in acetonitrile (440 mL) in an ice-water bath. The reaction mixture was warmed to room temperature and stirred overnight. To the mixture was added water (1350 mL). The precipitates formed were collected by filtration, washed with water and dried to give 1-(3-iodo-4-methoxyphenyl)ethanone (34) (70 g) with 86.5% yield.

Step B: A mixture of compound 34 (70.0 g, 254 mmol) and cuprous cyanide (34.0 g, 380 mmol) in DMF (400 mL) was stirred at 130° C. overnight. The reaction mixture was cooled to room temperature and filtered through a celite pad. To the filtrate was added water (1600 mL), and the mixture was extracted with ethyl acetate (800 mL×3). The combined organic layer was washed with water (40 mL×2) and brine (400 mL), dried over anhydrous sodium sulfate, filtered, and concentrated under vacuum to give 5-acetyl-2-methoxybenzonitrile (35) (50.0 g). The crude product was used directly in the next step without further purification.

Step C: To a solution of crude compound 35 (45.0 g) in methanol (250 mL) was added bromine (49.0 g, 307 mmol) in methanol (50 mL), and the resulting mixture was stirred at room temperature overnight. To the mixture was added water (900 mL) and the precipitate were collected by filtration, washed with water and dried to give 5-(2-bromoacetyl)-2-methoxybenzonitrile (36) (41.0 g). The total yield of steps B and C was 70.6%.

Step D: A mixture of compound 36 (41.0 g, 161 mmol) and compound 1 (24.0 g, 161 mmol) in toluene (600 mL) was stirred at reflux for 48 h. The reaction mixture was cooled to room temperature, diluted with water (400 mL), adjusted to pH 7-8 with saturated sodium bicarbonate, and extracted with dichloromethane (600 mL×3). The combined organic layer was dried over anhydrous sodium sulfate and concentrated under vacuum. The residue was purified by flash column chromatography on silica gel (eluted with ethyl acetate/petroleum ether=1:30-2:1) to afford 5-(2-ethylimidazo[1,2-a]pyridine-3-carbonyl)-2-methoxybenzonitrile (37) (25.7 g) with 52.3% yield.

Step E: Sodium hydride (60% dispersion in mineral oil, 4.8 g, 120 mmol) was added portionwise to a solution of ethanethiol (8.4 mL) in THF (30 mL). The reaction mixture was stirred for about 5 minutes and filtered. The cake was added into a solution of compound 37 (9.0 g, 29.5 mmol) in DMF (25 mL). The resulting mixture was stirred at 60° C. for 2 h, cooled to room temperature, and filtered through a celite pad. To the filtrate was added water (100 mL), and the mixture was adjusted to pH 5-6 with 2 M aqueous citric acid. The precipitates formed were collected by filtration, washed with water, and dried. The cake was crystallized from acetonitrile to give 5-(2-ethylimidazo[1,2-a]pyridine-3-carbonyl)-2-hydroxybenzonitrile (14) (7.2 g) with 83.8% yield.

Step F: To a solution of compound 14 (7.2 g, 24.7 mmol) in DMF (70 mL) was added N-bromosuccimide (5.28 g, 29.7 mmol) portionwise. After addition, the reaction mixture was stirred for another 1 h and diluted with water (210 mL). The precipitates were collected by filtration, washed with water and dried. The cake was crystallized from acetonitrile to give 3-bromo-5-(2-ethylimidazo[1,2-a]pyridine-3-carbonyl)-2-hydroxybenzonitrile (38) (7.0 g) with 76.8% yield. $^1$H NMR (DMSO-d6, 300 MHz) δ 9.01 (d, J=6.9 Hz, 1H), 8.02 (s, 1H), 7.83 (s, 1H), 7.78-7.75 (m, 1H), 7.65-7.59 (m, 1H), 7.22-7.17 (m, 1H), 2.58-2.50 (m, 2H), 1.19 (t, J=7.2 Hz, 3H). MS (EI, m/z): 368.0 [M−H]$^-$.

Example 16: Synthesis of 5-(2-ethylimidazo[1,2-a]pyridine-3-carbonyl)-2-hydroxy-3-iodobenzonitrile (39)

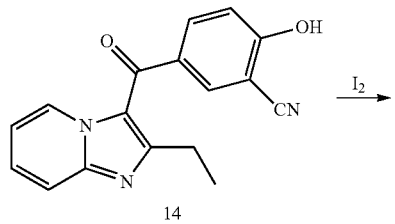

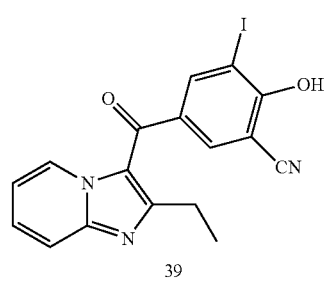

Using compound 14 as a starting material, compound 39 was prepared according to the procedure of example 10. $^1$H NMR (DMSO-d6, 500 MHz) δ 9.04 (d, J=7.0 Hz, 1H), 8.23 (d, J=1.5 Hz, 1H), 7.87 (s, 1H), 7.77 (d, J=8.5 Hz, 1H), 7.66-7.63 (m, 1H), 7.23-7.21 (m, 1H), 2.56-2.50 (m, 2H), 1.20 (t, J=7.5 Hz, 3H). MS (EI, m/z): 416.0 [M−H]⁻.

Example 17: Synthesis of 5-(2-ethylimidazo[1,2-a]pyridine-3-carbonyl)-3-fluoro-2-hydroxybenzonitrile (40)

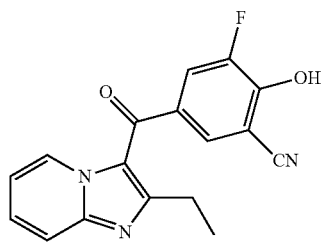

Compound 40 was prepared according to the procedures of steps A, B and C in example 11 and step C in example 14 by using 1-(3-fluoro-4-hydroxyphenyl)ethanone as an alternative reagent. $^1$H NMR (DMSO-d6, 300 MHz) δ 9.18 (d, J=6.9 Hz, 1H), 7.83-7.75 (m, 3H), 7.64-7.59 (m, 1H), 7.23-7.18 (m, 1H), 2.46-2.41 (m, 2H), 1.15 (t, J=7.2 Hz, 3H). MS (EI, m/z): 310.1[M+H]⁺.

Example 18: Synthesis of (3,5-dibromo-4-hydroxyphenyl)(2-propylimidazo[1,2-a]-pyridine-3-yl)methanone (41)

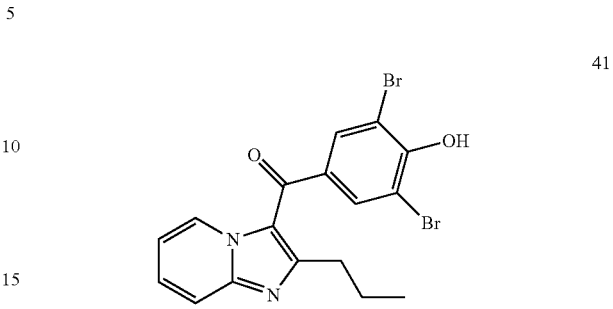

Compound 41 was prepared according to the procedure of example 1 by using butyryl chloride in step A. $^1$H NMR (DMSO-d6, 500 MHz) δ 10.81 (s, 1H), 9.18 (d, J=6.5 Hz, 1H), 7.86 (s, 2H), 7.73 (d, J=9.0 Hz, 1H), 7.61-7.58 (m, 1H), 7.19-7.17 (m, 1H), 2.38 (q, J=7.5 Hz, 2H), 1.68-1.63 (m, 2H), 0.76 (t, J=7.5 Hz, 3H). MS (EI, m/z): 436.9 [M−H]⁻.

Example 19: Synthesis of (2-ethylimidazo[1,2-a]pyridine-3-yl)(2-ethylsulfanyl-4-hydroxyphenyl)methanone (44)

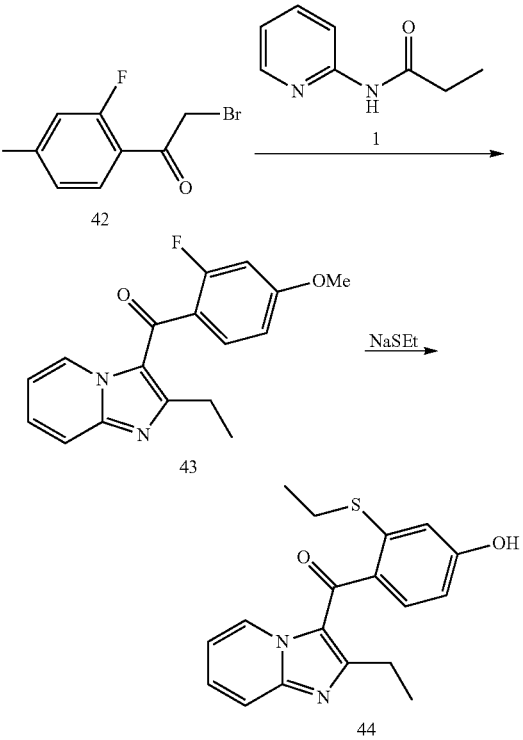

Compound 44 was prepared according to the procedures of steps B, C and D in example 12 by using 1-(2-fluoro-4-methoxyphenyl)ethanone as an alternative reagent. $^1$H NMR (DMSO-d6, 500 MHz) δ 10.08 (s, 1H), 9.42 (d, J=7.0 Hz, 1H), 7.74 (d, J=8.5 Hz, 1H), 7.63-7.59 (m, 1H), 7.27-7.20 (m, 2H), 6.88 (d, J=2.0 Hz, 1H), 6.68 (dd, J=2.0, 8.0 Hz, 1H), 2.88 (q, J=7.5 Hz, 2H), 2.26 (q, J=7.5 Hz, 2H), 1.16 (t, J=7.5 Hz, 3H), 1.05 (t, J=7.5 Hz, 3H). MS (EI, m/z): 325.1 [M−H]⁻.

Example 20: Synthesis of (3-bromo-5-chloro-4-hydroxyphenyl)(2-ethylimidazo[1,2-a]-pyridin-3-yl)methanone (45)

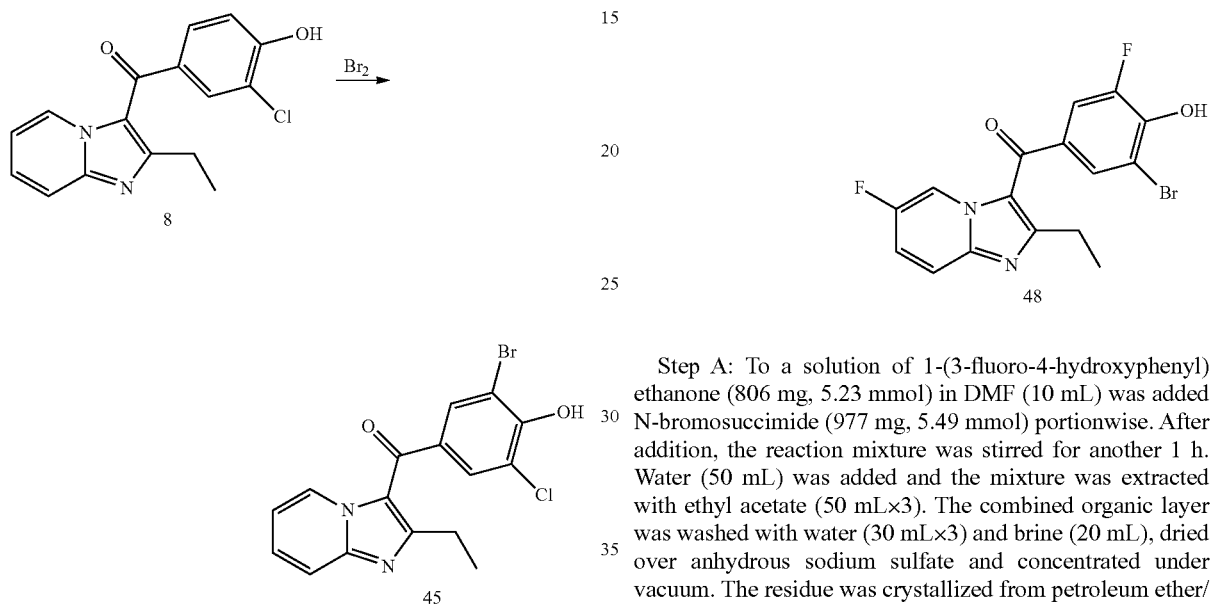

Using compound 8 as a starting material, compound 45 was prepared according to the procedure of step D in example 9. ¹H NMR (DMSO-d6, 500 MHz) δ 9.19 (d, J=6.5 Hz, 1H), 7.83 (d, J=2.0 Hz, 1H), 7.76-7.74 (m, 2H), 7.61-7.58 (m, 1H), 7.20-7.17 (m, 1H), 2.43 (q, J=7.5 Hz, 2H), 1.16 (t, J=7.5 Hz, 3H). MS (EI, m/z): 379.0 [M−H]⁻.

Example 21: Synthesis of (3-bromo-5-fluoro-4-hydroxyphenyl)(2-ethyl-6-fluoroimidazo-[1,2-a]pyridin-3-yl)methanone (48)

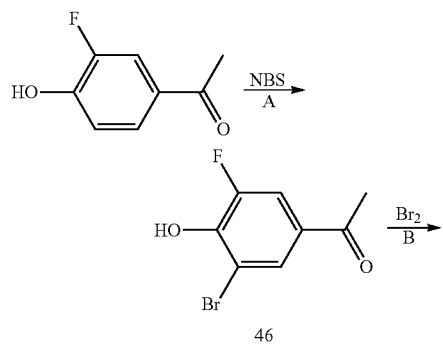

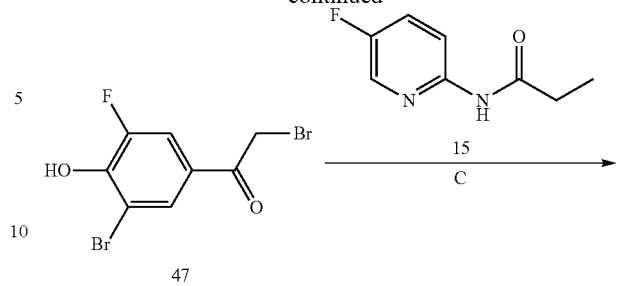

Step A: To a solution of 1-(3-fluoro-4-hydroxyphenyl)ethanone (806 mg, 5.23 mmol) in DMF (10 mL) was added N-bromosuccimide (977 mg, 5.49 mmol) portionwise. After addition, the reaction mixture was stirred for another 1 h. Water (50 mL) was added and the mixture was extracted with ethyl acetate (50 mL×3). The combined organic layer was washed with water (30 mL×3) and brine (20 mL), dried over anhydrous sodium sulfate and concentrated under vacuum. The residue was crystallized from petroleum ether/ethyl acetate to get 1-(3-bromo-5-fluoro-4-hydroxy-phenyl)ethanone (46) (1.0 g) with 82.0% yield.

Step B: To a solution of compound 46 (1.0 g, 4.29 mmol) in methanol (20 mL) was added bromine (824 mg, 5.16 mmol) in methanol (5 mL), and the mixture was stirred at room temperature overnight, quenched with water (60 mL), and extracted with ethyl acetate (60 mL×3). The combined organic layer was washed with brine (30 mL), dried over anhydrous sodium sulfate and concentrated under vacuum. The residue was purified by flash column chromatography on silica gel (eluted with ethyl acetate/petroleum ether=1:5) to afford 2-bromo-1-(3-bromo-5-fluoro-4-hydroxyphenyl)-ethanone (47) (940 mg) with 70.2% yield.

Step C: A mixture of compound 15 (210 mg, 1.25 mmol) and compound 47 (300 mg, 0.962 mmol) in 1-methyl-2-pyrrolidinone (10 mL) was stirred at 150° C. overnight. The reaction mixture was cooled to room temperature and water (50 mL) was added. The mixture was adjusted to pH 7-8 with 2 M aqueous citric acid and extracted with dichloromethane (50 mL×3). The combined organic layer was dried over anhydrous sodium sulfate and concentrated under vacuum. The residue was purified by flash column chromatography on silica gel (eluted with ethyl acetate/petroleum ether=1:25-1:5) to afford (3-bromo-5-fluoro-4-hydroxyphenyl)(2-ethyl-6-fluoroimidazo[1,2-a]-pyridin-3-yl)methanone (48). ¹H NMR (DMSO-d6, 500 MHz) δ 11.44 (s, 1H), 9.24-9.22 (m, 1H), 7.88-7.85 (m, 1H), 7.75-7.71 (m, 2H), 7.63-7.60 (m, 1H), 2.47 (q, J=7.5 Hz, 2H), 1.18 (t, J=7.5 Hz, 3H). MS (EI, m/z): 379.0 [M−H]⁻.

Example 22: Synthesis of (2-ethyl-6-fluoroimidazo[1,2-a]pyridin-3-yl)(3-fluoro-4-hydroxy-5-iodophenyl)methanone (51)

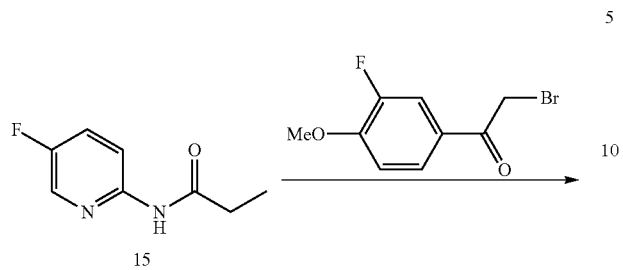

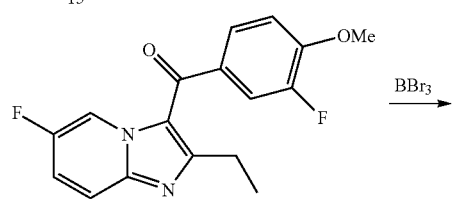

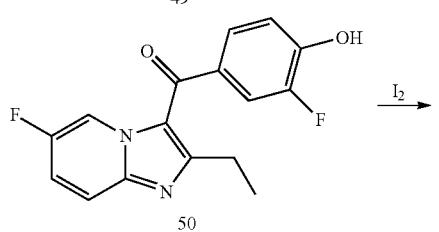

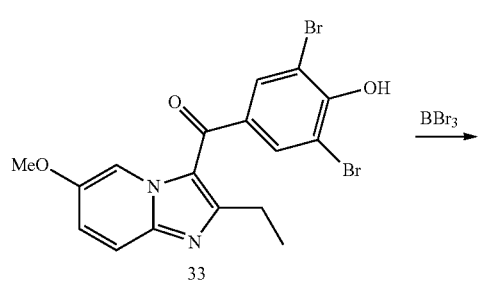

Using compound 15 as the starting material, compound 51 was prepared according to the procedures of steps B and C in example 9, followed by the procedure in example 10. $^1$H NMR (DMSO-d6, 300 MHz) δ 11.44 (s, 1H), 9.19-9.17 (m, 1H), 7.86-7.81 (m, 2H), 7.73-7.66 (m, 1H), 7.60-7.56 (m, 1H), 2.49-2.41 (m, 2H), 1.16 (t, J=7.5 Hz, 3H). MS (EI, m/z): 427.1 [M−H]$^-$.

Example 23: Synthesis of (3,5-dibromo-4-hydroxyphenyl)(2-ethyl-6-hydroxyimidazo-[1,2-a]pyridin-3-yl)methanone (52)

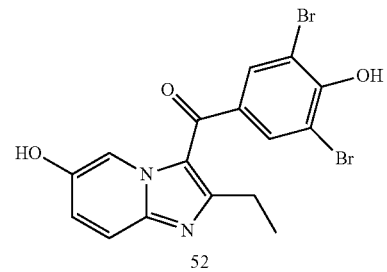

Using compound 33 as the starting material, compound 52 was prepared according to the procedure of step C in example 1. $^1$H NMR (DMSO-d6, 400 MHz) δ 10.00 (s, 1H), 8.92 (s, 1H), 7.84 (s, 2H), 7.63 (d, J=9.6 Hz, 1H), 7.31-7.29 (m, 1H), 2.37 (q, J=7.6 Hz, 2H), 1.13 (t, J=7.6 Hz, 3H). MS (EI, m/z): 441.0 [M+H]$^+$.

Example 24: Synthesis of (6-bromo-2-ethyl-7-methylimidazo[1,2-a]pyridin-3-yl)-(3,5-dibromo-4-hydroxyphenyl)methanone (56)

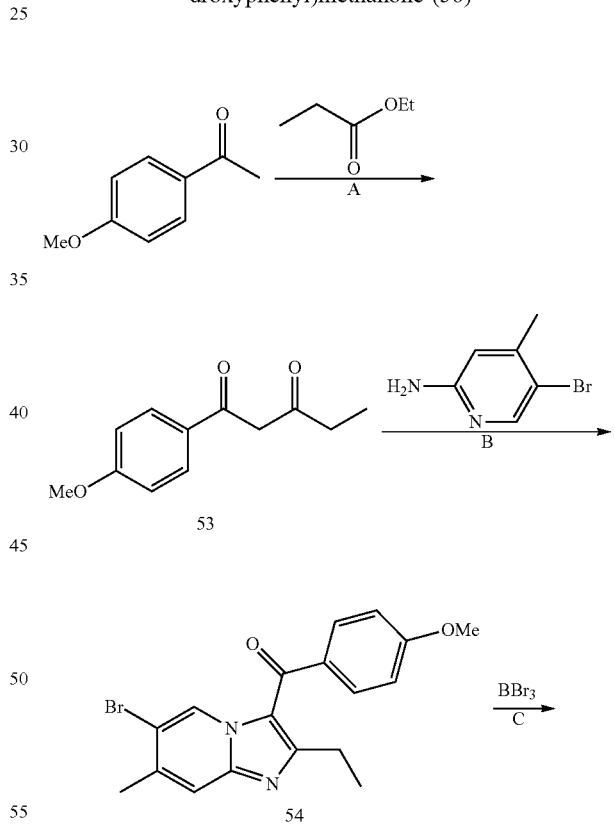

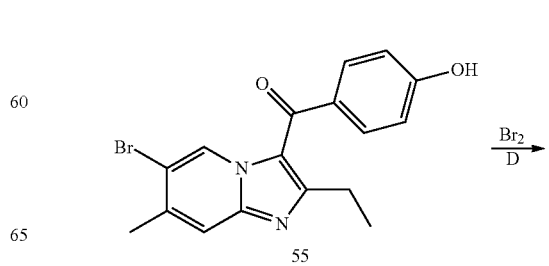

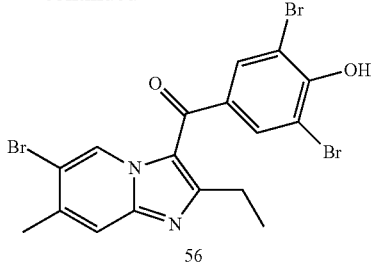

56

Step A: Sodium hydride (60% dispersion in mineral oil, 1.68 g, 42 mmol) was added portionwise to a solution of 1-(4-methoxyphenyl)ethanone (3.0 g, 20.0 mmol) in DMF (15 mL) at −10-0° C. The mixture was stirred at this temperature for another 40 minutes, and ethyl propionate was added (2.04 g, 20 mmol). The reaction mixture was stirred at room temperature overnight, diluted with water (60 mL), and extracted with ethyl acetate (30 mL×3). The combined organic layer was washed with brine (20 mL×2), dried over anhydrous sodium sulfate, and concentrated under vacuum. The residue was purified by flash column chromatography on silica gel (eluted with ethyl acetate/petroleum ether=1:30) to get 1-(4-methoxyphenyl)pentane-1,3-dione (53) (3.16 g) with 76.6% yield.

Step B: To a solution of 5-bromo-4-methylpyridin-2-amine (187 mg, 1.0 mmol) and compound 53 (247 mg, 1.2 mmol) in THF (6 mL) was added (diacetoxyiodo)benzene (386 mg, 1.2 mmol) and boron trifluoride ether (28 mg, 0.2 mmol) in an ice-water bath. After addition, the reaction mixture was stirred at room temperature overnight and diluted with water (30 mL). The mixture was adjusted to pH 7-8 with saturated sodium bicarbonate and extracted with ethyl acetate (30 mL×3). The combined organic layer was washed with brine (20 mL), dried over anhydrous sodium sulfate and concentrated under vacuum. The residue was purified by flash column chromatography on silica gel (eluted with ethyl acetate/petroleum ether=1:30) to get (6-bromo-2-ethyl-7-methylimidazo-[1,2-a]pyridin-3-yl)(4-methoxyphenyl)methanone (54) (120 mg) with 32.2% yield.

Methods used in steps C and D of example 1 were followed in steps C and D to afford (6-bromo-2-ethyl-7-methylimidazo[1,2-a]pyridin-3-yl)(3,5-dibromo-4-hydroxyphenyl)methanone (56). ¹H NMR (DMSO-d6, 400 MHz) δ 9.35 (s, 1H), 7.86 (s, 2H), 7.80 (s, 1H), 2.41 (q, J=7.6 Hz, 2H), 1.16 (t, J=7.6 Hz, 3H). MS (EI, m/z): 518.9 [M+H]⁺.

Example 25: Synthesis of (3,5-dibromo-4-hydroxyphenyl)(2-ethyl-7-(trifluoromethyl)-imidazo[1,2-a]pyridin-3-yl)methanone (57)

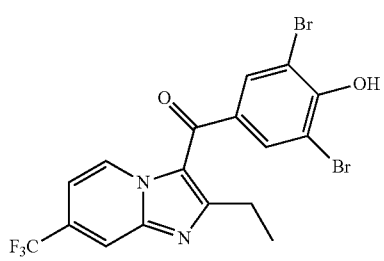

57

Using 5-(trifluoromethyl)pyridin-2-amine as the starting material, compound 57 was prepared according to the procedure of step B in example 25 and the procedures of steps C and D in example 1. ¹H NMR (DMSO-d6, 400 MHz) δ 9.23 (d, J=7.2 Hz, 1H), 8.27 (s, 1H), 7.93 (s, 2H), 7.45 (dd, J=2.0, 7.2 Hz, 1H), 2.50-2.48 (m, 2H), 1.20 (t, J=7.2 Hz, 3H). MS (EI, m/z): 492.9 [M+H]⁺.

Example 26: Synthesis of 3-(3,5-dibromo-4-hydroxybenzoyl)-2-ethylimidazo[1,2-a]-pyridine-6-carbonitrile (58)

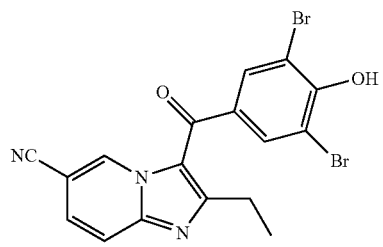

58

Using 6-aminonicotinonitrile as the starting material, compound 58 was prepared according to the procedure of step B in example 25 and the procedures of steps C and D in example 1. ¹H NMR (DMSO-d6, 400 MHz) δ 9.56-9.55 (m, 1H), 7.92-7.89 (m, 3H), 7.86-7.83 (m, 1H), 2.48-2.46 (m, 2H), 1.22-1.17 (m, 3H). MS (EI, m/z): 450.0 [M+H]⁺.

Example 27: Synthesis of (2-deuterium-4-hydroxyphenyl)(2-ethylimidazo[1,2-a]-pyridine-3-yl)methanone (62) and (2-deuterium-3,5-dibromo-4-hydroxyphenyl)-(2-ethylimidazo[1,2-a]pyridine-3-yl)methanone (63)

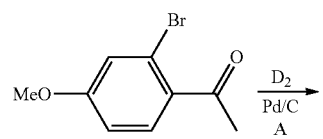

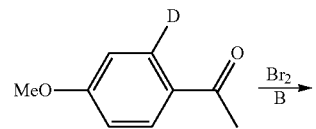

59

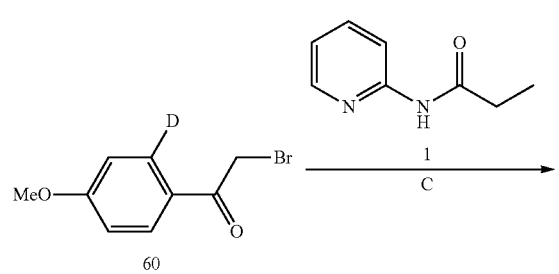

60

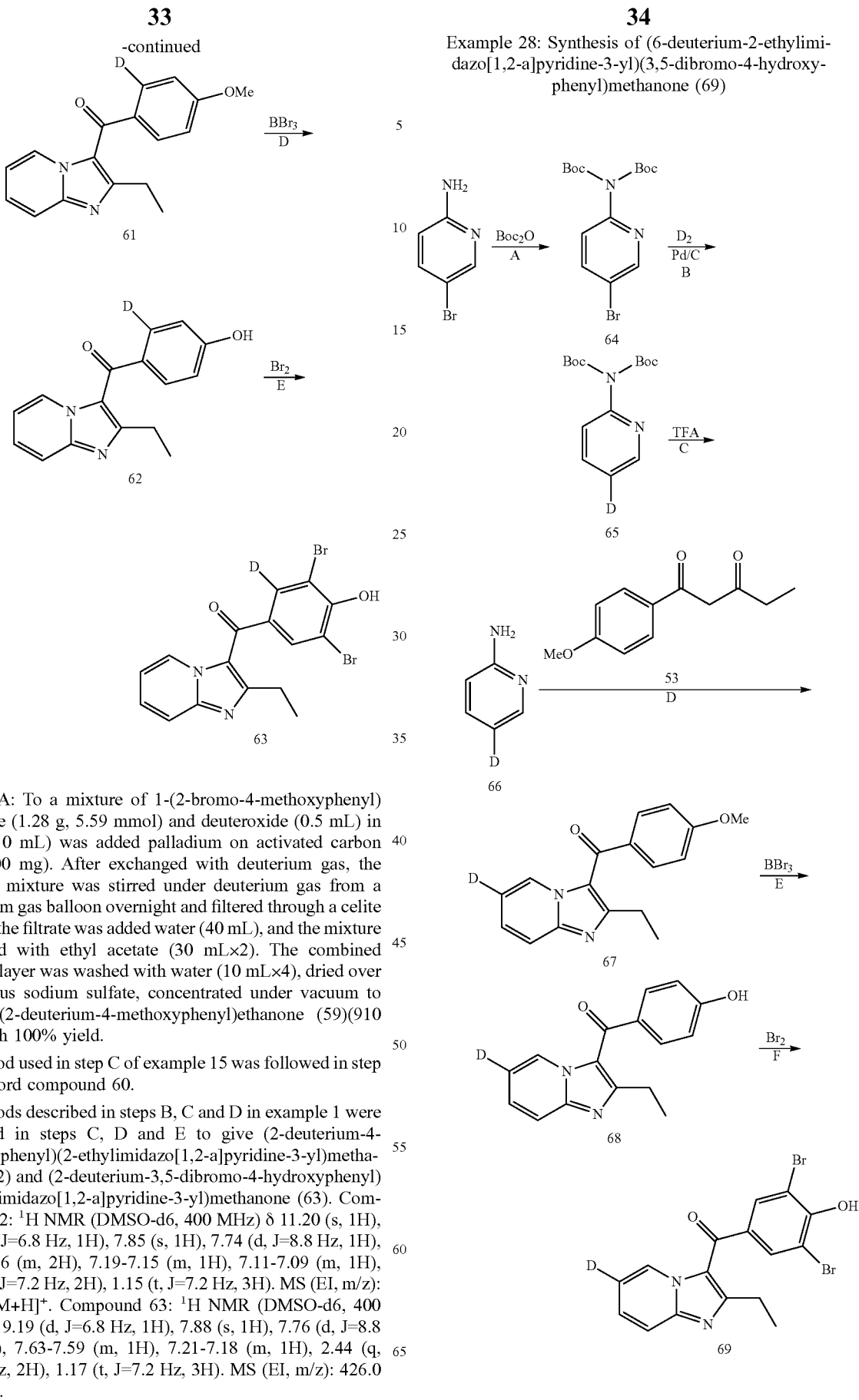

Example 28: Synthesis of (6-deuterium-2-ethylimidazo[1,2-a]pyridine-3-yl)(3,5-dibromo-4-hydroxyphenyl)methanone (69)

Step A: To a mixture of 1-(2-bromo-4-methoxyphenyl)ethanone (1.28 g, 5.59 mmol) and deuteroxide (0.5 mL) in DMF (10 mL) was added palladium on activated carbon (5%, 100 mg). After exchanged with deuterium gas, the reaction mixture was stirred under deuterium gas from a deuterium gas balloon overnight and filtered through a celite pad. To the filtrate was added water (40 mL), and the mixture extracted with ethyl acetate (30 mL×2). The combined organic layer was washed with water (10 mL×4), dried over anhydrous sodium sulfate, concentrated under vacuum to give 1-(2-deuterium-4-methoxyphenyl)ethanone (59)(910 mg) with 100% yield.

Method used in step C of example 15 was followed in step B to afford compound 60.

Methods described in steps B, C and D in example 1 were followed in steps C, D and E to give (2-deuterium-4-hydroxyphenyl)(2-ethylimidazo[1,2-a]pyridine-3-yl)methanone (62) and (2-deuterium-3,5-dibromo-4-hydroxyphenyl)(2-ethylimidazo[1,2-a]pyridine-3-yl)methanone (63). Compound 62: $^1$H NMR (DMSO-d6, 400 MHz) δ 11.20 (s, 1H), 9.16 (d, J=6.8 Hz, 1H), 7.85 (s, 1H), 7.74 (d, J=8.8 Hz, 1H), 7.61-7.56 (m, 2H), 7.19-7.15 (m, 1H), 7.11-7.09 (m, 1H), 2.46 (q, J=7.2 Hz, 2H), 1.15 (t, J=7.2 Hz, 3H). MS (EI, m/z): 268.2 [M+H]$^+$. Compound 63: $^1$H NMR (DMSO-d6, 400 MHz) δ 9.19 (d, J=6.8 Hz, 1H), 7.88 (s, 1H), 7.76 (d, J=8.8 Hz, 1H), 7.63-7.59 (m, 1H), 7.21-7.18 (m, 1H), 2.44 (q, J=7.2 Hz, 2H), 1.17 (t, J=7.2 Hz, 3H). MS (EI, m/z): 426.0 [M+H]$^+$.

Step A: A mixture of 5-bromopyridin-2-amine (5.19 g, 30.0 mmol), ethyldiisopropylamine (8.58 g, 66.4 mmol), 4-dimethylaminopyridine (366 mg, 3.0 mmol) and di-tert-butyl dicarbonate (14.4 g, 66.0 mmol) in dichloromethane (30 mL) was stirred at room temperature overnight. The reaction mixture was concentrated under vacuum. The residue was purified by flash column chromatography on silica gel (eluted with ethyl acetate/petroleum ether=1:20-1:3) to get imidodicarbonic acid (2-(4-bromo-2-pyridinyl)-1,3-bis (1,1-dimethylethyl))ester (64) (5.38 g) with 48.0% yield.

Step B: To a mixture of compound 64 (5.59 g, 15.0 mmol), DMF (25 mL) and deuteroxide (0.5 mL) was added palladium on activated carbon (5%, 200 mg). After exchanged with deuterium gas, the mixture was stirred under deuterium gas from a balloon for 48 h. The reaction mixture was filtered through a celite pad. To the filtrate was added water (100 mL), and the mixture extracted with ethyl acetate (50 mL×3). The combined organic layer was washed with water (30 mL×3), dried over anhydrous sodium sulfate, and concentrated under vacuum. The residue was purified by flash column chromatography on silica gel (eluted with ethyl acetate/petroleum ether=1:40-1:1) to get imidodicarbonic acid (2-(4-deuterium-2-pyridinyl)-1,3-bis(1,1-dimethylethyl))ester (65) (2.70 g) with 60.9% yield.

Step C: A mixture of compound 65 (2.69 g, 9.11 mmol), trifluoroacetic acid (4 mL) and water (0.5 mL) in dichloromethane (20 mL) was stirred at room temperature overnight. To the reaction mixture was added water (30 mL), and the mixture was adjusted pH 8-9 with 2 M aqueous sodium hydroxide and extracted with ethyl acetate (40 mL×3). The combined organic layer was dried over anhydrous sodium sulfate and concentrated under vacuum. The residue was purified by flash column chromatography on silica gel (eluted with ethyl acetate/petroleum ether=1:10-1:1) to get 2-amino-4-deuterium-pyridine (66) (676 mg) with 78.0% yield.

Methods described in steps B, C and D in example 25 were followed in steps D, E and F the to give (6-deuterium-2-ethylimidazo[1,2-a]pyridine-3-yl)(3,5-dibromo-4-hydroxyphenyl)methanone (69). $^1$H NMR (DMSO-d6, 400 MHz) δ 9.20-9.19 (m, 1H), 7.88 (s, 2H), 7.77-7.75 (m, 1H), 7.64-7.59 (m, 1H), 2.43 (q, J=7.6 Hz, 2H), 1.16 (t, J=7.6 Hz, 3H). MS (EI, m/z): 426.0 [M+H]$^+$.

Example 29: Synthesis of (2-cyclopropylimidazo[1,2-a]pyridin-3-yl)(3,5-dibromo-4-hydroxyphenyl) methanone (73)

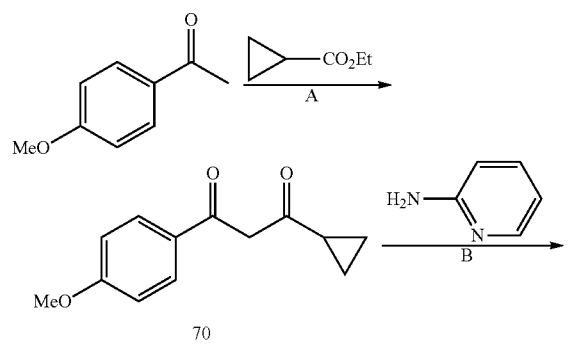

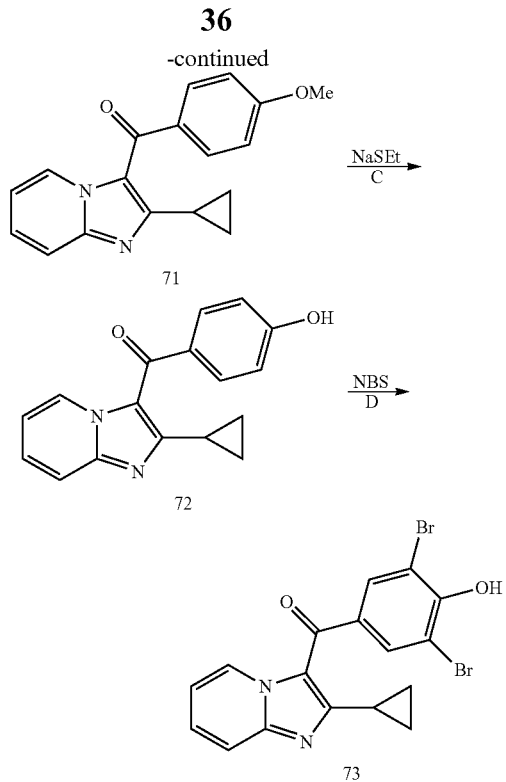

Using ethyl cyclopropanecarboxylate as the starting material, compound 71 was prepared according to the procedures of steps A and B in example 24. $^1$H NMR (DMSO-d6, 400 MHz) δ 9.24-9.23 (m, 1H), 7.81-7.79 (m, 2H), 7.68-7.65 (m, 1H), 7.58-7.56 (m, 1H), 7.16-7.09 (m, 3H), 3.87 (s, 3H), 1.56-1.54 (m, 1H), 1.08-1.06 (m, 2H), 0.88-0.85 (m, 2H).

Method used in step E in example 15 was followed in step C to give (2-cyclopropylimidazo[1,2-a]pyridin-3-yl)(4-hydroxyphenyl)methanone (72). $^1$H NMR (DMSO-d6, 400 MHz) δ 9.17-9.16 (m, 1H), 7.72-7.70 (m, 2H), 7.66-7.64 (m, 1H), 7.55-7.51 (m, 1H), 7.14-7.10 (m, 1H), 6.91-6.89 (m, 2H), 1.62-1.60 (m, 1H), 1.07-1.05 (m, 2H), 0.88-0.85 (m, 2H).

Method used in step F of example 15 was followed in step D to give (2-cyclopropylimidazo-[1,2-a]pyridin-3-yl)(3,5-dibromo-4-hydroxyphenyl)methanone (73). $^1$H NMR (DMSO-d6, 400 MHz) δ 9.25-9.23 (m, 1H), 7.97 (s, 2H), 7.70-7.68 (m, 1H), 7.61-7.57 (m, 1H), 7.20-7.16 (m, 1H), 1.58-1.55 (m, 1H), 1.13-1.10 (m, 2H), 0.94-0.89 (m, 2H). MS (EI, m/z): 437.0 [M+H]$^+$.

Example 30: Synthesis of 3-bromo-5-(2-ethylimidazo[1,2-a]pyridine-3-carbonyl)-2-hydroxybenzonitrile hydrogen chloride (74)

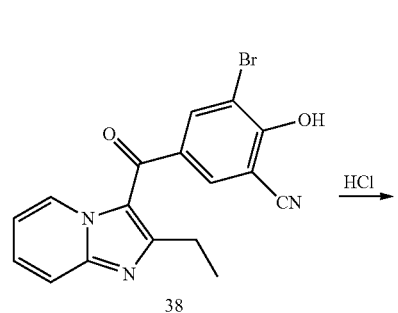

-continued

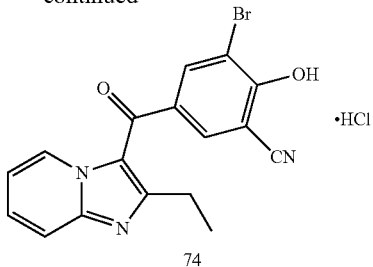

74

A mixture of compound 38 (970 mg, 2.62 mmol) in ethyl acetate (200 mL) was stirred under reflux for 20 min to give a clear solution, then cooled to room temperature, bubbled with hydrogen chloride for about 5 minutes. The precipitates formed were collected by filtration to give 3-bromo-5-(2-ethylimidazo[1,2-a]-pyridine-3-carbonyl)-2-hydroxybenzonitrile hydrogen chloride (74) (794 mg) with 74.5% yield. $^1$H NMR (DMSO-d6, 300 MHz) δ 9.12 (d, J=6.9 Hz, 1H), 8.22 (d, J=2.1 Hz, 1H), 8.09 (d, J=2.1 Hz, 1H), 7.99-7.91 (m, 2H), 7.50-7.45 (m, 1H), 2.57 (q, J=7.5 Hz, 2H), 1.23 (t, J=7.5 Hz, 3H). MS (EI, m/z): 368.0 [M−H]$^-$.

Example 31: Synthesis of 5-(2-ethylimidazo[1,2-a]pyridine-3-carbonyl)-2-hydroxy-3-iodobenzonitrile hydrogen chloride (75)

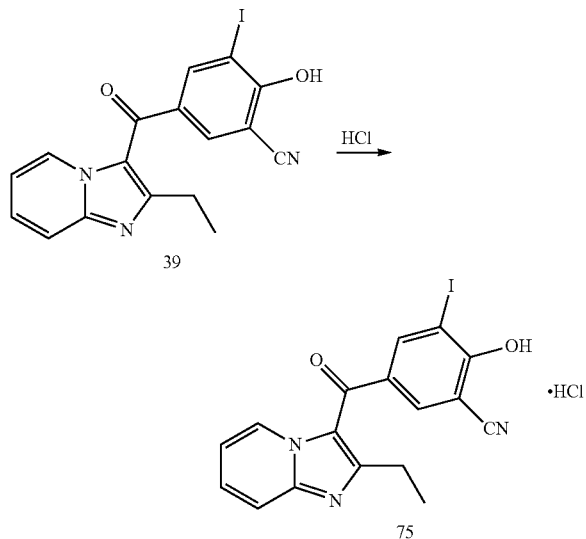

Using compound 39 as the starting material, compound 75 was prepared followed the same procedure as example 30. $^1$H NMR (DMSO-d6, 300 MHz) δ 9.11 (d, J=6.9 Hz, 1H), 8.41 (d, J=1.8 Hz, 1H), 8.11 (d, J=2.1 Hz, 1H), 8.02-7.95 (m, 2H), 7.54-7.49 (m, 1H), 2.59 (q, J=7.5 Hz, 2H), 1.25 (t, J=7.5 Hz, 3H). MS (EI, m/z): 416.0 [M−H]$^-$.

Example 32: Inhibition assay of uric acid transport for compounds in HEK293-hURAT1 transfection cell line 1. Materials Benzbromarone was purchased from Sigma-Aldrich Co. LLC. Plasmid pCMV6-hURAT1 was purchased from Origene Technologies, Inc. G418 was purchased from Sangon Biotech (Shanghai) Co., Ltd. HEK293 cell line was purchased from Cell Resource Center of Shanghai Institutes for Biological Sciences of the Chinese Academy of Sciences. $^{14}$C-Uric acid was purchased from American Radiolabeled Chemicals, Inc. Sodium gluconate, potassium gluconate, calcium gluconate, KH$_2$PO$_4$, MgSO$_4$, glucose, and HEPES were purchased from Sinopharm Chemical Reagent Co., Ltd. DMEM culture medium and fetal bovine serum were purchased from Thermo Fisher Scientific Inc.

2. Experimental Methods 2.1 Construction of a HEK293 stable cell line with high expression of hURAT1: The plasmid pCMV6-hURAT1 was transfected into HEK293 cells, then the stable strain was obtained by the G418 (final concentration 500 μg/mL) resistance screening, which is the high expression of hURAT1 transporter membrane protein. It can be used for in vitro inhibition assay of uric acid transporter hURAT1. (Weaver Y M, Ehresman D J, Butenhoff J L, et al. Roles of rat renal organic anion transporters in transporting perfluorinated carboxylates with different chain lengths. Toxicological Sciences, 2009, 113(2):305-314)

2.2 To a coated 24-well plate was added 200 μL of 0.1 mg/mL poly-lysine per well and the plate was left overnight. Poly-lysine was removed from wells. The wells were cleaned thoroughly with aseptic water and dried for use.

2.3 To the above coated 24 well plate was added HEK293-hURAT1 stable cells (2×10$^5$ cells per well). The cells was cultured at 37° C. under 5% CO$_2$ for 3 days.

2.4 The preparation of HBSS buffer: weighed following reagents according to the final concentration of 125 mM sodium gluconate, 4.8 mM potassium gluconate, 1.3 mM calcium gluconate, 1.2 mM KH$_2$PO$_4$, 1.2 mM MgSO$_4$, 5.6 mM glucose, and 25 mM HEPES with deionized water. The solution was fully mixed to give HBSS buffer (pH value: 7.4). The buffer was stored at −20° C.

2.5 The HBSS buffer was warmed to 37° C. in a water bath. Washed cells with HBSS twice, added 160 μL of HBSS and 20 μL test compound per well. The final concentration of tested compound per well is 500 nM. The blank control well contains only 180 μL of HBSS without tested compound. The plate was placed at room temperature for 30 min.

2.6 To each well was added 20 μL of 50 μM $^{14}$C-Uric acid. The plate was placed at room temperature for 20 min.

2.7 The solution in each well was removed and the cells in each well were washed with pre-cooled HBSS buffer. To each well was added 0.2 M NaOH to dissolve the cells. The solution containing cell fragments was collected and the right amount of scintillation liquid was added. The radioisotope intensity of the $^{14}$C-Uric acid (CPM value) was then detected by using PerkinElmer MicroBeta Trilux 1450 liquid scintillation analyzer.

2.8 All tests were repeated three times, and the results were averaged and the standard deviation (SD) was calculated. The formula for calculating the inhibitory rate of uric acid transport for compounds was shown as below:

$$InhibitoryRate\ (\%) = \frac{CPM\ of\ Blank\ control\ well - CPM\ of\ Test\ compound\ well}{CPM\ of\ Blank\ control\ well} \times 100\%$$

3. Test Results

The inhibitory rates of uric acid transport for compounds 4, 5, 9, 11, 12, 18, 19, 29, 30, 33, 38, 39, 41, 45, 51, 52, 56, 69, 74, 75, and benzbromarone at 500 nM were obtained according to the above experimental procedures. The tested results were listed in table 1. The results showed that in comparison with the control drug benzbromarone, the compounds have equal or better inhibitory effect of uric acid transport in HEK293-hURAT1 transfection cell line.

TABLE 1

Inhibitory rates of uric acid transport for test compounds and benzbromarone at 500 nM in HEK293-hURAT1 transfection cell line

| Compound number or drug | Inhibitory rates of uric acid transport, ±SD (%) |
|---|---|
| BBR | 55.57 ± 1.42 |
| 4 | 71.68 ± 1.84 |
| 5 | 63.00 ± 3.33 |
| 9 | 60.63 ± 0.82 |
| 11 | 63.55 ± 0.95 |
| 12 | 56.24 ± 0.12 |
| 18 | 65.44 ± 0.71 |
| 19 | 68.84 ± 2.83 |
| 29 | 64.35 ± 0.12 |
| 30 | 68.05 ± 1.49 |
| 33 | 65.06 ± 0.39 |
| 38 | 62.41 ± 0.72 |
| 39 | 64.12 ± 2.25 |
| 41 | 55.53 ± 1.02 |
| 45 | 62.93 ± 3.34 |
| 51 | 61.32 ± 1.10 |
| 52 | 57.50 ± 3.61 |
| 56 | 62.80 ± 9.34 |
| 69 | 71.10 ± 2.50 |
| 74 | 62.75 ± 5.73 |
| 75 | 62.58 ± 0.84 |

BBR: benzbromarone.

Example 33: Cytotoxicity Test of Compounds on the Human Normal Liver Cell Lines L-02 and WRL-68

It has been reported that benzbromarone has a serious hepatotoxicity. Therefore, benzbromarone was used as a positive control drug in this assay. The cytotoxicity of the compounds on two human normal liver cell lines L-02 and WRL-68 was tested, respectively.

1. Materials

The human normal liver cell line L-02 was purchased from Procell Life Science & Technology Co., Ltd. The human normal liver cell line WRL-68 was given by the Life Science Institute of Nanjing University. Benzbromarone, Resazurin, and Methylene blue were purchased from Sigma-Aldrich Co. LLC. Potassium ferricyanide and potassium ferrocyanide were purchased from Aladdin (Shanghai) Biological Technology Co., Ltd. DMEM culture medium, phenol red free DMEM culture medium, and fetal bovine serum were purchased from Thermo Fisher Scientific Inc. Penicillin and streptomycin were purchased from Beyotime Biotechnology Co., Ltd.

2. Experimental Methods 2.1 The normal liver cell lines L-02 and WRL-68 were cultured with DMEM culture medium (containing 10% of fetal bovine serum, 100 U/mL of penicillin and 0.1 mg/mL of streptomycin) in an incubator under 5% $CO_2$ at 37° C. until the cell density was about 90%, respectively.

2.2 The cells were inoculated to a 96-well plate at a cell population of $1\times10^3$/well and then cultured in an incubator under 5% $CO_2$ at 37° C. for 24 h.

2.3 Tested compounds and benzbromarone at different concentration gradients were prepared by using the DMEM culture medium and added into wells at 100 μL/well as compounds wells. The DMEM culture medium was added into wells at 100 μL/well without tested compound as negative control wells. All plates were placed in an incubator under 5% $CO_2$ at 37° C. for 120 h.

2.4 Resazurin (15 mg/50 mL, 200×), Methylene Blue (25 mg/10 mL, 1000×), Potassium ferricyanide (0.329 g/100 mL, 100×) and Potassium ferrocyanide (0.422 g/100 mL, 100×) were dissolved into PBS (0.1 M, pH=7.4) to obtain 10× Alamar Blue solution for standby. This 10× Alamar Blue solution was diluted into 1× Alamar Blue solution with phenol red free DMEM culture medium before use.

2.5 The cells were washed with PBS (0.1 M, pH=7.4) twice. The Alamar Blue solution was added into wells at 100 μL/well. 100 μL of Alamar Blue solution was added into wells without cells to serve as blank control wells. The 96-well plate was placed in an incubator under 5% $CO_2$ at 37° C. for 3 h. Each concentration of compound was repeated three times during the test.

2.6 The fluorescence value of the cells was detected at Ex 530/Em 590 nm by ELISA Victor X4 (Perkin Elmer). The fluorescence value of the cells containing compound is the $F_{(test\ compound)}$; the fluorescence value of the cells without compound as blank control is the $F_{(blank\ control)}$; the fluorescent value of the cells from negative control group is $F_{(negative\ control)}$. The average value and standard deviation of cell viability of three repeated concentrations was calculated by the following formula:

$$\text{Cell viability (\%)} = \frac{F_{(test\ compound)} - F_{(blank\ control)}}{F_{(negative\ control)} - F_{(blank\ control)}} \times 100\%$$

2.7 The half inhibitory concentration ($IC_{50}$) of the compound for the cells L-02 and WRL-68 was obtained from the cell viability by Prism Graph software.

3. Test Results

The half inhibitory concentration ($IC_{50}$) of compounds 4, 5, 9, 18, 33, 38, 39, 45, 51, 52, 56, 69, 74, and 75 against the human normal liver cell lines L-02 and WRL-68 are greater than 100 μM. The $IC_{50}$ of Benzbromarone for L-02 and WRL-68 was 40.17 μM and 45.54 μM, respectively.

Example 34: Uric Acid Excretion Test of Compound 74 in Hyperuricemia Mice

1. Materials 1.1 Preparation of Tested Compound 74 and Benzbromarone

To compound 74 or benzbromarone was added certain amount of 0.5% CMC-Na solution and the mixture was stirred at room temperature to obtain a suspension based on the designed dosage, respectively.

1.2 Animals

Species: Kingming mice (Clean Level); body weights: 25 to 30 g; ages: 4 to 5 weeks; sex: male. These mice were purchased from Shanghai SLAC Laboratory Animal Co., Ltd. Certificate No.: SCXK (HU) 2012-2002. Animal quality certificate number: 2015000522173.

1.3 Reagents

Yeast extract powder was purchased from Beijing Aoxing Biology Co., Ltd. Adenine and potassium oxonate were purchased from Aladdin (Shanghai) Biological Technology Co., Ltd. CMC-Na was purchased from Sinopharm Chemical Reagent Co., Ltd. Uric acid assay kit (phosphotungstic acid method) was purchased from Nanjing Jiancheng Bioengineering Institute.

2. Experimental Methods 2.1 Preparation of a Mixed Suspension of Yeast Extract and Adenine A certain amount of adenine and yeast extract powder was weighted and a certain amount of double distilled water was added. The mixture was stirred at about 60° C. for 40 min to give a suspension, which the concentration of yeast extract is 0.6 g/mL and the concentration of adenine is 12 mg/mL.

2.2 Preparation of Potassium Oxonate Suspension

A suspension of 20 mg/mL potassium oxonate was prepared by mixing a certain amount of potassium oxonate with 0.5% CMC-Na solution before use.

2.3 the Establishment of Hyperuricemia Mice Model and Administration of Tested Materials Male Kunming mice were randomly divided into four groups: blank control group, model group, compound 74 group, and benzbromarone group. Each group has six mice. All mice fasted 2 to 3 h before use. The model group, benzbromarone group, and compound 74 group were orally given a suspension of yeast extract and adenine prepared above to reach the final dosage of 10 g/kg (body weight) of yeast extract and 200 mg/kg (body weight) of adenine, respectively. The blank control group was only given same volume of normal saline orally. After 2.5 h, all mice in compound 74 group and benzbromarone group were given 10 mL/kg of suspension of compound 74 (1.5 mg/mL) and 10 mL/kg of suspension of benzbromarone (1.5 mg/mL), respectively. The blank control group and model group were orally given same volume of 0.5% CMC-Na solution. All animals were treated in the same way for seven days by using administration methods described above. On the last day, after administration of a suspension of yeast extract and adenine for the model group, compound 74 group, and benzbromarone group, all mice in these three groups were given 12.5 mL/kg of potassium oxonate (20 mg/mL) by i.p. The blank control was only given same volume of 0.5% CMC-Na solution by i.p. After 30 min, compound 74 and benzbromarone were administrated orally to the mice at same dosages as above in compound 74 group and benzbromarone group, respectively. The blank control group and model group were orally given same volume of 0.5% CMC-Na solution.

2.3 Sample Collection and Analysis

Collection of urine samples: All mice were placed in metabolic cages with normal diet individually after giving test compounds on the last day. 24 h urine was collected and the urine volume was measured. The urine was centrifugated at 3000 rpm for 20 min and the supernatant was collected.

Detection of the concentration of uric acid of mice urine samples: uric acid concentration in samples was detected by using uric acid assay kit (phosphotungstic acid method) followed the procedures described in the instruction.

3. Test Results

The results of promoting uric acid excretion in hyperuricemia mice were listed in table 2. Both compound 74 and benzbromarone significantly increased uric acid excretion in hyperuricemia mice. The efficacy of compound 74 in promotion of uric acid excretion was significantly better than benzbromarone. Compared with the model group of hyperuricemia mice, the uric acid excretion of compound 74 was increased by about 46.77%, while the excretion of uric acid excretion of benzbromarone was increased by about 25.35%.

TABLE 2

Uric acid excretion test of compound 74 and benzbromarone by oral administration in hyperuricemia mice

| Group | Mice numbers | Dose (mg/kg) | Uric acid in urine for 24 h, ±SD (mmol) | Changes of uric acid excretion (compared with model group, %) |
| --- | --- | --- | --- | --- |
| Blank control | 6 | / | 6.80 ± 2.17 | 63.61 |
| Model | 6 | / | 10.69 ± 1.48## | 100 |
| BBR | 6 | 15 | 13.40 ± 1.59* | 125.35 |
| Compound 74 | 6 | 15 | 15.69 ± 1.53**▲ | 146.77 |

The excretion change of uric acid amount in the model group is set to 100%.
vs. blank control group, ##means: $P < 0.01$.
vs. model group, *means: $P < 0.05$, **means: $P < 0.01$.
vs. Benzbromarone group, ▲means: $P < 0.05$.

Example 35: Study on Acute Toxicity of Single Dose of Compound 74 in Rats

1. Materials 1.1 Preparation of Tested Compound 74 and Benzbromarone

Compound 74 and benzbromarone were ground, and certain amount of 0.5% CMC-Na solution was added to prepare a suspension, respectively, before use. Benzbromarone was purchased from Mianyang Kaixing Pharmaceutical Technology Co., Ltd. Lot Number is BXML-201506005.

1.2 Animals

Species: SD rats (SPF Level); body weights: 120 to 180 g; ages: 5 to 6 weeks. Source: purchased from Animal Research Center of Wuhan University; certificate No.: SCXK (E) 2014-0004; animal quality certificate number: 2015000522173.

2. Experimental Methods and Results

In the pre-experiment of acute toxicity in rats, the highest dose at 5 g/kg of compound 74 did not cause death of rats. Therefore, the dosage of compound 74 was determined to be 5 g/kg in this assay. When the dose of benzbromarone was 0.14 g/kg in the pre-experiment, no death of rats was found. Therefore, the dosage of benzbromarone was determined to be 0.14 g/kg in this assay.

Rats were randomly divided into group A1, group B1 and blank control group. Each group has 10 of rats with half male and half female. A single dose of compound 74 suspension, benzbromarone suspension, and 0.5% CMC-Na solution at 20 mL/kg was given by oral administration to group A1, group B1, and blank control group, respectively, after 6 h of fasting.

The dosage and death rate of every group were shown in table 3. No immediate toxicity was found in each group and delayed toxicity was not found in the observation period from 24 h to 14 days. All rats survived and were in good condition with weight gain. The weight changes were listed in table 4. The maximum tolerated dose of compound 74 and benzbromarone in acute toxicity test were 5 g/kg and 0.14 g/kg, respectively.

TABLE 3

The dosage and death rate of SD rats in each group

| Group | Sample | Dosage (g/kg) | Sample quantity (mg) | Volume (mL) | Concentration (mg/mL) | Death rate |
|---|---|---|---|---|---|---|
| A1 | 74 | 5.0 | 7520.9 | 30.0 | 250 | 0/10 |
| B1 | BBR | 0.14 | 272.2 | 38.9 | 7 | 0/10 |

Each group has 10 rats.

TABLE 4

Weight changes of SD rats in each group

| Sample | No. and sex of rats | 0 day ($\bar{X} \pm SD$) (g) | 7 day ($\bar{X} \pm SD$) (g) | 14 day ($\bar{X} \pm SD$) (g) | Weight gain rate (%) |
|---|---|---|---|---|---|
| 74 | 5 (M) | 149.06 ± 5.95 | 204.04 ± 21.69 | 258.12 ± 17.65 | +73.2 |
|    | 5 (F) | 135.94 ± 5.62 | 183.02 ± 11.10 | 208.04 ± 11.90 | +53.0 |
| BBR | 5 (M) | 149.36 ± 3.25 | 207.80 ± 8.72 | 273.88 ± 13.54 | +83.4 |
|     | 5 (F) | 139.04 ± 6.60 | 175.00 ± 6.24 | 201.30 ± 19.84 | +44.8 |
| blank control | 5 (M) | 147.64 ± 4.48 | 191.16 ± 13.65 | 248.34 ± 23.13 | +68.2 |
|               | 5 (F) | 134.20 ± 4.07 | 173.28 ± 9.27 | 204.44 ± 15.70 | +52.3 |

"Weight gain rate" means the weight of rats in 14 day compared with 0 day, and "+" means the weight was increased.

Example 36: Study on Pharmacokinetics of Compound 74 Following Intravenous and Oral Administration in SD Rats 1. Materials 1.1 Preparation of Solution of Tested Compound 74

Dose formulation preparation for PO: Weight out the required amount of compound 74. Added approximately 70% of 0.5% CMC-Na with stirring, vortexing and sonication to mix well until visually well suspension. Then added the remaining vehicle to target total volume and vortex-mix.

Dose formulation preparation for IV: Weight out the required amount of compound 74. Added appropriate DMSO with sonication until dissolved, then added appropriate HP-β-Cyclodextrin water solution (20%, w/v) with vortexing to mix well.

1.2 Animals

Species: SD rats (SPF Level); sex: male; source: Sino-British SIPPR/BK Lab Animal Ltd., Shanghai.

2. Methods 2.1 Dose and Administration

The animals that dosed via orally were fasted overnight (10-14 hours) prior to oral administration. Food supply to the animals dosed orally were resumed 4 h post-dose. Dose administration information is presented in table 5.

TABLE 5

The dosage of compound to SD rats

| Sample | Group | Weight (g) | Dosage (mg/kg) | Concentration (mg/mL) | Volume (mL) | Route of Administration |
|---|---|---|---|---|---|---|
| 74 | A-1 | 188.2 | 10 | 1 | 1.9 | Oral (PO) |
|    |     | 197.3 |    |   | 2.0 |           |
|    |     | 213.0 |    |   | 2.1 |           |
|    | A-2 | 207.8 | 1  | 0.2 | 1.0 | Intravenous (IV) |
|    |     | 221.1 |    |     | 1.1 |                  |
|    |     | 220.9 |    |     | 1.1 |                  |

2.2 Sample Collection and Bioanalysis

Blood samples (approximately 250 μL/sample) were collected via jugular vein at Pre-dose and Post-dose (5 min, 15 min, 30 min, 1 h, 2 h, 4 h, 6 h, 8 h, and 24 h). Blood samples were placed into tubes containing sodium heparin and centrifuged conditions at 8000 rpm for 6 minutes at 2-8° C. to separate plasma from the samples. Plasma sample (50 μL) were transferred to tube, then 250 μL IS solution (200 ng/mL Tolbutamide) was added to it. After vortexing for 1 min and centrifuging for 5 min at 15000 rpm, 200 μL aliquots of supernatant were transferred to 96-well plate for LC-MS/MS analysis. The calibration curve of compound 74 was ranging from 1 to 1000 ng/mL. The LLOQ is 1 ng/mL for plasma.

2.3 Pharmacokinetic Analysis

A non-compartmental module of WinNonlin® Professional 5.2 was used to calculate parameters. The bioavailability was calculated as F %=(Dose$_{(IV)}$×AUC$_{(0-t)(PO)}$)/(Dose$_{(PO)}$×AUC$_{(0-t)(IV)}$)×100%.

3. Results

The pharmacokinetic parameters of the SD rats with compound 74 obtained from the above methods are shown in table 6. Compound 74 of this invention has good pharmacokinetic parameters and high bioavailability in SD rats.

TABLE 6

Pharmacokinetics Parameters of compound 74 in SD rats following oral administration and intravenous administration

| | oral administration (PO: 10 mg/kg) | | | | | |
|---|---|---|---|---|---|---|
| Rats No. | $t_{1/2}$ (h) | $T_{max}$ (h) | $C_{max}$ (ng/mL) | $AUC_{(0-t)}$ (ng/mL*h) | $MRT_{(0-\infty)}$ (h) | F* (%) |
| 101 | 2.70 | 2.00 | 8251.74 | 89284.20 | 6.00 | 100.28 |
| 102 | 2.90 | 2.00 | 9205.06 | 89890.12 | 5.90 | 100.96 |
| 103 | 3.00 | 6.00 | 6976.14 | 96188.83 | 6.80 | 108.04 |
| Mean | 2.90 | 3.30 | 8144.31 | 91787.72 | 6.30 | 103.09 |
| SD | 0.10 | 2.30 | 1118.34 | 3823.50 | 0.50 | 4.29 |

TABLE 6-continued

Pharmacokinetics Parameters of compound 74 in SD rats following oral administration and intravenous administration

| | intravenous administration (IV: 1 mg/kg) | | | | | | |
|---|---|---|---|---|---|---|---|
| Rats No. | $t_{1/2}$ (h) | $T_{max}$ (h) | $C_{max}$ (ng/mL) | $AUC_{(0-t)}$ (ng/mL*h) | Vz (mL/kg) | Clz (mL/h/kg) | $MRT_{(0-\infty)}$ (h) |
| 201 | 5.40 | 0.10 | 5494.59 | 8786.13 | 858.55 | 110.23 | 5.40 |
| 202 | 6.00 | 0.10 | 6705.53 | 9076.84 | 917.79 | 105.66 | 5.60 |
| 203 | 6.00 | 0.10 | 6885.21 | 8847.27 | 934.49 | 108.65 | 5.40 |
| Mean | 5.80 | 0.10 | 6361.78 | 8903.41 | 903.61 | 108.18 | 5.50 |
| SD | 0.30 | 0.00 | 756.36 | 153.27 | 39.90 | 2.32 | 0.10 |

*Obtained from $AUC_{(0-t)}$

What is claimed is:

1. A compound having a general chemical Formula (I)

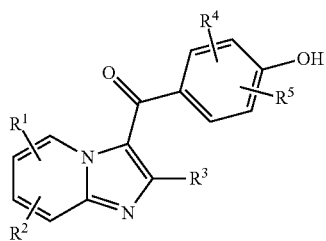

(I)

or a pharmaceutically acceptable salt thereof, wherein:
$R^1$ and $R^2$ are independently selected from the group consisting of hydrogen, deuterium, halogen, cyano, hydroxyl, $C_{1-5}$ alkyl, substituted $C_{1-5}$ alkyl, $C_{1-3}$ alkoxy, substituted $C_{1-3}$ alkoxy, $C_{1-3}$ alkylthio, or substituted $C_{1-3}$ alkylthio in one or more;
$R^3$ is selected from the substituted or unsubstituted group consisting of $C_{1-4}$ alkyl or $C_{3-4}$ cycloalkyl, and its substituents are selected from the group consisting of deuterium, halogen, $C_{1-2}$ alkyl or $C_{3-4}$ cycloalkyl;
$R^4$ and $R^5$ are independently selected from the group consisting of halogen, cyano, $C_{2-3}$ alkenyl, $C_{2-3}$ alkynyl, $C_{1-3}$ alkyl, substituted $C_{1-3}$ alkyl, $C_{1-3}$ alkoxy, substituted $C_{1-3}$ alkoxy, $C_{1-3}$ alkylthio, or substituted $C_{1-3}$ alkylthio; wherein the substituents in $R^1$, $R^2$, $R^4$, and $R^5$ are independently selected from deuterium, halogen, $C_{1-3}$ alkyl, $C_{3-4}$ cycloalkyl or $C_{1-3}$ alkoxy.

2. The compound of claim 1 or a pharmaceutically acceptable salt thereof, wherein:
$R^1$ and $R^2$ are independently selected from the group consisting of hydrogen, deuterium, fluorine, chlorine, bromine, cyano, hydroxyl, $C_{1-3}$ alkyl, substituted $C_{1-3}$ alkyl, $C_{1-3}$ alkoxy, or substituted $C_{1-3}$ alkoxy; Wherein the substituents are independently selected from the group consisting of deuterium, halogen, $C_{1-3}$ alkyl, $C_{3-4}$ cycloalkyl or $C_{1-3}$ alkoxy.

3. The compound of claim 2 or a pharmaceutically acceptable salt thereof, wherein:
$R^1$ and $R^2$ are independently selected from the group consisting of hydrogen, deuterium, fluorine, chlorine, bromine, CN, $C_{1-3}$ alkyl, $C_{1-3}$ halogenated alkyl or $C_{1-3}$ alkoxy.

4. The compound of claim 1 or a pharmaceutically acceptable salt thereof, wherein:
$R^3$ is selected from the substituted or unsubstituted group consisting of $C_{1-3}$ alkyl and $C_{3-4}$ cycloalkyl; Wherein the substituents are independently selected from the group consisting of deuterium, halogen, $C_{1-2}$ alkyl or $C_{3-4}$ cycloalkyl.

5. The compound of claim 1, wherein:
$R^4$ and $R^5$ are independently selected from the group consisting of halogen, cyano, ethylene, acetylene, $C_{1-2}$ alkyl, substituted $C_{1-2}$ alkyl, $C_{1-2}$ alkoxy, substituted $C_{1-2}$ alkoxy, $C_{1-2}$ alkylthio, or substituted $C_{1-2}$ alkylthio; Wherein the substituents are independently selected from the group consisting of deuterium, halogen, $C_{1-2}$ alkyl, $C_{3-4}$ cycloalkyl or $C_{1-3}$ alkoxy.

6. The compound of claim 1, wherein:
$R^4$ and $R^5$ are independently selected from the group consisting of halogen, cyano, $C_{1-2}$ alkyl, $C_{1-2}$ halogenated alkyl, $C_{1-2}$ alkoxy or $C_{1-2}$ alkylthio.

7. The compound of claim 1, wherein the compound is selected from the group consisting of:
(3,5-Dibromo-4-hydroxyphenyl)(2-ethylimidazo[1,2-a]pyridin-3-yl)methanone;
(2-Ethylimidazo[1,2-a]pyridine-3-yl)(4-hydroxy-3,5-diiodophenyl)methanone;
(3-Chloro-4-hydroxyphenyl)(2-ethylimidazo[1,2-a]pyridin-3-yl)methanone;
3-Chloro-5-(2-ethylimidazo[1,2-a]pyridine-3-carbonyl)-2-hydroxybenzonitrile;
(3-Bromo-4-hydroxy-5-iodophenyl)(2-ethylimidazo[1,2-a]pyridine-3-yl)methanone;
(2-Ethylimidazo[1,2-a]pyridine-3-yl)(4-hydroxy-3-iodo-5-methylphenyl)methanone;
(3-Bromo-5-chloro-4-hydroxyphenyl)(2-ethyl-6-fluoroimidazo[1,2-a]pyridine-3-yl)methanone;
(3-Chloro-4-hydroxy-5-iodophenyl)(2-ethyl-6-fluoroimidazo[1,2-a]pyridine-3-yl)methanone;
5-(2-Ethylimidazo[1,2-a]pyridine-3-carbonyl)-2-hydroxy-3-methylbenzonitrile;
(3-Bromo-4-hydroxy-5-(trifluoromethyl)phenyl)(2-ethylimidazo[1,2-a]-pyridine-3-yl)methanone;
(3,5-Dibromo-4-hydroxyphenyl)(2-ethyl-6-methylimidazo[1,2-a]pyridine-3-yl)methanone;
(3,5-Dibromo-4-hydroxyphenyl)(2-ethyl-6-methoxyimidazo[1,2-a]pyridine-3-yl)methanone;
(2-Ethylimidazo[1,2-a]pyridin-3-yl)(2-(ethylthio)-4-hydroxyphenyl)methanone;
3-Bromo-5-(2-ethylimidazo[1,2-a]pyridine-3-carbonyl)-2-hydroxybenzonitrile;
5-(2-Ethylimidazo[1,2-a]pyridine-3-carbonyl)-2-hydroxy-3-iodobenzonitrile;
5-(2-Ethylimidazo[1,2-a]pyridine-3-carbonyl)-3-fluoro-2-hydroxybenzonitrile;
(3,5-Dibromo-4-hydroxyphenyl)(2-propylimidazo[1,2-a]pyridine-3-yl)methanone;

(3-Bromo-5-chloro-4-hydroxyphenyl)(2-ethylimidazo[1,2-a]pyridin-3-yl)methanone;
(3-Bromo-5-fluoro-4-hydroxyphenyl)(2-ethyl-6-fluoroimidazo[1,2-a]pyridin-3-yl)methanone;
(2-Ethyl-6-fluoroimidazo[1,2-a]pyridin-3-yl)(3-fluoro-4-hydroxy-5-iodophenyl)methanone;
(3,5-Dibromo-4-hydroxyphenyl)(2-ethyl-6-hydroxyimidazo[1,2-a]pyridin-3-yl)methanone;
(6-Bromo-2-ethyl-7-methylimidazo[1,2-a]pyridin-3-yl)(3,5-dibromo-4-hydroxyphenyl)-methanone;
(3,5-Dibromo-4-hydroxyphenyl)(2-ethyl-7-(trifluoromethyl)imidazo[1,2-a]pyridin-3-yl)-methanone;
3-(3,5-Dibromo-4-hydroxyphenyl)-2-ethylimidazo[1,2-a]pyridine-6-carbonitrile;
(6-Deuterium-2-ethylimidazo[1,2-a]pyridine-3-yl)(3,5-dibromo-4-hydroxyphenyl)methanone;
(2-Cyclopropylimidazo[1,2-a]pyridin-3-yl)(3,5-dibromo-4-hydroxyphenyl)methanone;
3-Bromo-5-(2-ethylimidazo[1,2-a]pyridine-3-carbonyl)-2-hydroxybenzonitrile hydrogen chloride; and
5-(2-Ethylimidazo[1,2-a]pyridine-3-carbonyl)-2-hydroxy-3-iodobenzonitrile hydrogen chloride.

8. A pharmaceutical acceptable composition comprising the compound of claim 1 or its pharmaceutically acceptable salt as active ingredient, and a pharmaceutically acceptable carrier.

9. A method for treating a hyperuricemia or a gout comprising a step of administrating to a subject in need a therapeutically effective amount of the compound of claim 1 or its pharmaceutically acceptable salt.

* * * * *